United States Patent
McFarland et al.

(10) Patent No.: US 10,384,204 B2
(45) Date of Patent: Aug. 20, 2019

(54) SYSTEMS FOR OPERATING ELECTROKINETIC DEVICES

(71) Applicant: Berkeley Lights, Inc., Emeryville, CA (US)

(72) Inventors: Andrew W. McFarland, Berkeley, CA (US); Daniele Malleo, El Cerrito, CA (US); J. Tanner Nevill, El Cerrito, CA (US); Russell A. Newstrom, Alameda, CA (US); Keith J. Breinlinger, San Rafael, CA (US); Paul M. Lundquist, San Francisco, CA (US); Justin K. Valley, Berkeley, CA (US); Jonathan Cloud Dragon Hubbard, Pasadena, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 481 days.

(21) Appl. No.: 14/963,759

(22) Filed: Dec. 9, 2015

(65) Prior Publication Data
US 2016/0193604 A1    Jul. 7, 2016

Related U.S. Application Data

(60) Provisional application No. 62/259,460, filed on Nov. 24, 2015, provisional application No. 62/089,834, filed on Dec. 10, 2014.

(51) Int. Cl.
*B01L 3/00*    (2006.01)
*B01L 9/00*    (2006.01)
(Continued)

(52) U.S. Cl.
CPC ..... *B01L 3/50273* (2013.01); *B01L 3/502715* (2013.01); *B01L 9/527* (2013.01);
(Continued)

(58) Field of Classification Search
CPC ....... B01L 3/50273; B01L 3/5027; B01L 3/50
(Continued)

(56) References Cited

U.S. PATENT DOCUMENTS

| 4,701,415 A | 10/1987 | Dutton |
| 6,174,675 B1 | 1/2001 | Chow et al. |

(Continued)

FOREIGN PATENT DOCUMENTS

| WO | WO 2010147078 | 12/2010 |
| WO | WO 20160172454 | 10/2016 |

OTHER PUBLICATIONS

PCT International Search Report and Written Opinion for International Application No. PCT/US2015/064690, Applicant Berkeley Lights, Inc., forms PCT/ISA/210, 220, and 237, dated Jun. 8, 2016 (20 pages).
(Continued)

*Primary Examiner* — Christine T Mui
(74) *Attorney, Agent, or Firm* — Vista IP Law Group LLP

(57) ABSTRACT

A system for operating an electrokinetic device includes a support configured to hold and operatively couple with the electrokinetic device, an integrated electrical signal generation subsystem configured to apply a biasing voltage across a pair of electrodes in the electrokinetic device, and a light modulating subsystem configured to emit structured light onto the electrokinetic device. The system can further include a thermally controlled flow controller, and/or be configured to measure impedance across the electrokinetic device. The system can be a light microscope, including an optical train. The system can further include a light pipe, which can be part of the light modulating subsystem, and which can be configured to supply light of substantially uniform intensity to the light modulating subsystem or directly to the optical train.

24 Claims, 16 Drawing Sheets

(51) Int. Cl.
| | |
|---|---|
| *G02B 21/08* | (2006.01) |
| *G02B 27/14* | (2006.01) |
| *G01N 27/447* | (2006.01) |
| *G02B 21/26* | (2006.01) |
| *G02B 21/32* | (2006.01) |
| *G02B 21/36* | (2006.01) |
| *G02B 27/09* | (2006.01) |
| *G02B 27/10* | (2006.01) |
| *G02B 19/00* | (2006.01) |

(52) U.S. Cl.
CPC . *G01N 27/44721* (2013.01); *G01N 27/44791* (2013.01); *G02B 21/082* (2013.01); *G02B 21/26* (2013.01); *G02B 21/32* (2013.01); *G02B 21/361* (2013.01); *G02B 27/141* (2013.01); *G02B 27/145* (2013.01); *B01L 2200/027* (2013.01); *B01L 2200/0647* (2013.01); *B01L 2200/14* (2013.01); *B01L 2300/06* (2013.01); *B01L 2300/0645* (2013.01); *B01L 2300/0654* (2013.01); *B01L 2300/12* (2013.01); *B01L 2300/1822* (2013.01); *B01L 2300/1827* (2013.01); *B01L 2400/0415* (2013.01); *B01L 2400/0424* (2013.01); *B01L 2400/0427* (2013.01); *B01L 2400/0677* (2013.01); *G02B 19/0028* (2013.01); *G02B 27/0994* (2013.01); *G02B 27/1006* (2013.01)

(58) Field of Classification Search
USPC .......................................... 422/502, 500, 50
See application file for complete search history.

(56) References Cited

U.S. PATENT DOCUMENTS

| | | | |
|---|---|---|---|
| 6,294,063 B1 | 9/2001 | Becker | |
| 6,942,776 B2 | 9/2005 | Medoro | |
| 6,958,132 B2 | 10/2005 | Chiou et al. | |
| 7,090,759 B1 | 8/2006 | Seul | |
| 7,294,249 B2* | 11/2007 | Gawad .............. | B01L 3/502761 204/547 |
| 9,134,513 B2 | 9/2015 | Chen | |
| 9,144,806 B2 | 9/2015 | Chen | |
| 2001/0050276 A1 | 12/2001 | Inami | |
| 2003/0008364 A1 | 1/2003 | Wang | |
| 2004/0191789 A1 | 9/2004 | Manaresi et al. | |
| 2005/0112548 A1 | 5/2005 | Segawa | |
| 2005/0173313 A1* | 8/2005 | Tyvoll ................ | G01N 15/1056 209/644 |
| 2005/0175981 A1 | 8/2005 | Voldman | |
| 2005/0266571 A1 | 12/2005 | Stout et al. | |
| 2006/0091015 A1 | 5/2006 | Lau | |
| 2006/0154361 A1 | 7/2006 | Wikswo | |
| 2007/0056646 A1 | 3/2007 | Dourdeville et al. | |
| 2007/0095669 A1* | 5/2007 | Lau ......................... | B03C 5/005 204/547 |
| 2008/0006535 A1 | 1/2008 | Paik et al. | |
| 2008/0013092 A1 | 1/2008 | Maltezos | |
| 2008/0302732 A1 | 12/2008 | Soh | |
| 2009/0170186 A1 | 7/2009 | Wu et al. | |
| 2010/0000620 A1 | 1/2010 | Fouillet | |
| 2010/0101960 A1 | 4/2010 | Ohta et al. | |
| 2010/0273681 A1 | 10/2010 | Cerrina | |
| 2012/0024708 A1 | 2/2012 | Chiou et al. | |
| 2012/0118740 A1 | 5/2012 | Garcia et al. | |
| 2012/0148140 A1 | 6/2012 | Di Carlo | |
| 2012/0325665 A1 | 12/2012 | Chiou | |
| 2013/0118901 A1 | 5/2013 | Pollack et al. | |
| 2013/0118905 A1 | 5/2013 | Morimoto | |
| 2013/0261021 A1 | 10/2013 | Bocchi | |
| 2014/0116881 A1 | 5/2014 | Chapman et al. | |
| 2014/0124370 A1 | 5/2014 | Short | |
| 2015/0151298 A1 | 6/2015 | Hobbs et al. | |
| 2015/0306598 A1 | 10/2015 | Khandros et al. | |
| 2015/0306599 A1 | 10/2015 | Khandros et al. | |
| 2016/0160259 A1 | 6/2016 | Du | |
| 2016/0171686 A1 | 6/2016 | Du et al. | |
| 2016/0252495 A1 | 9/2016 | Ricicova | |
| 2016/0312165 A1 | 10/2016 | Lowe | |

OTHER PUBLICATIONS

PCT Invitation to Pay Additional Fees for International Publication No. PCT/2015/064690, Applicant Berkeley Lights, Inc., Form PCT/ISA/206, dated Mar. 11, 2016 (10 pages).

Chiou et al., Massively parallel manipulation of single cells and microparticles using optical images, Nature 436:370-73 (Jul. 21, 2005).

Chiou, Pei-Yu, Massively parallel optical manipulation of cells, micro- and nano-particles on optoelectronic devices, Dissertation, University of California at Berkeley, Fall 2005 (147 pages).

Hsu et al., Sorting of Differentiated Neurons using Phototransistor-based Optoelectronic Tweezers for Cell Replacement Therapy of Neurodegenerative Diseases, IEEE Conference on Transducers (Jun. 21-25, 2009).

Valley et al., Optoelectronic Tweezers as a Tool for Parallel Single-Cell Manipulation and Stimulation, IEEE Transactions on Biomedical Circuits and Systems 3(6):424-30 (2009). Dec. 1, 2009.

Xu, Guolin et al,. Recent Trends in Dielectrophoresis, Informacije MIDEM, 2010, vol. 40, Issue No. 4, pp. 253-262. Sep. 15, 2010.

Liu et al., Optofluidic control using photothermal nanoparticles, Nature Materials 5:27-32(2006). Dec. 18, 2005.

Hung et al., Continuous Perfusion Microfluidic Cell Culture Array for High-Throughput Cell-Based Assays, Biotech and Bioengineering 89(1): 1-8 (2004). Dec. 3, 2004.

Yi, Microfluidics technology for manipulation and analysis of biological cells, Analytica Chimica Acta 560:1-23 (2006). Jan. 25, 2006.

Invitation to Respond to Written Opinion and attached Search Report and Written Opinion, dated Jul. 31, 2018, for Singapore Patent Application No. 11201704659P, Applicant Berkeley Lights, Inc., 13 pages.

* cited by examiner

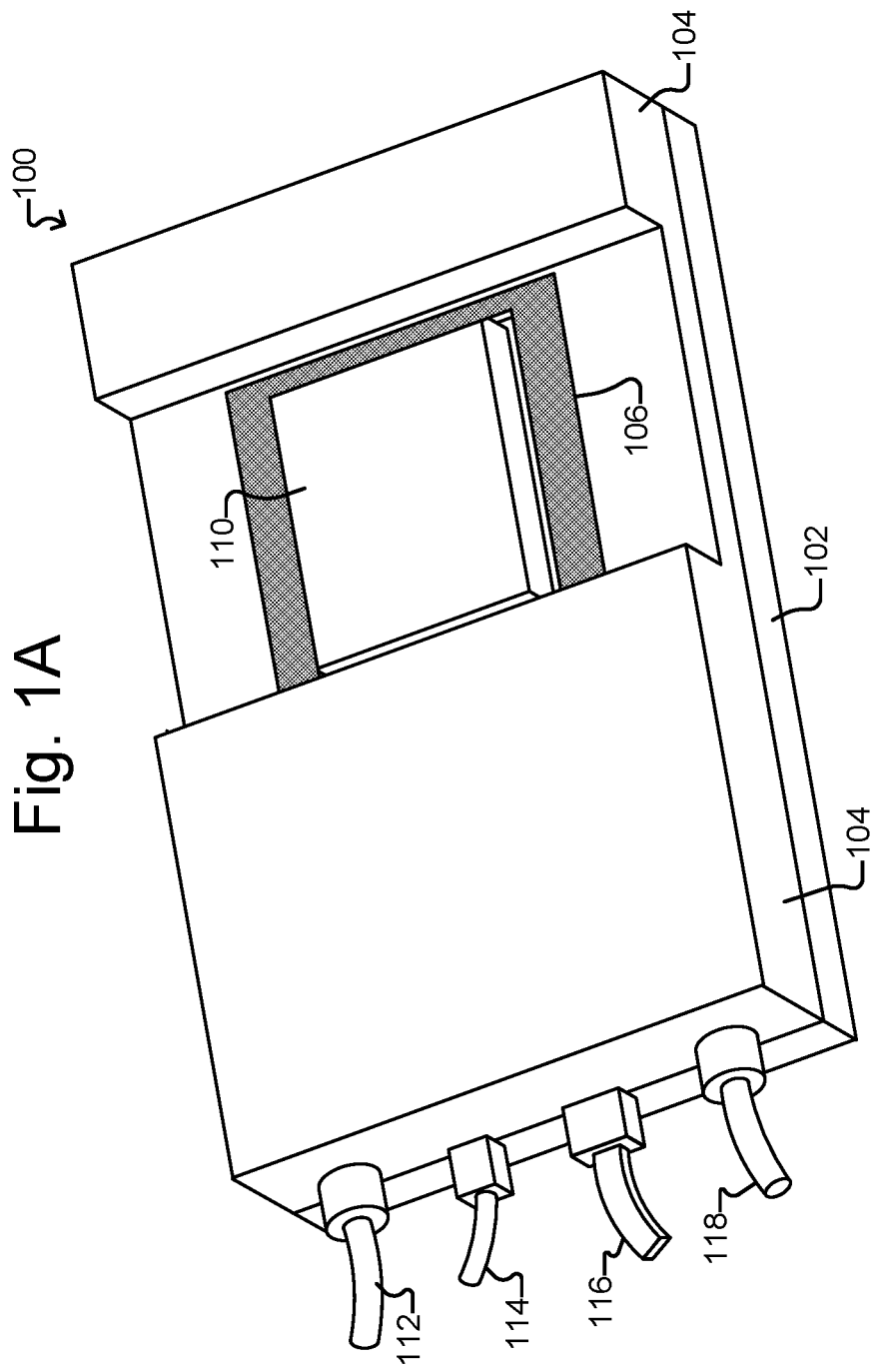

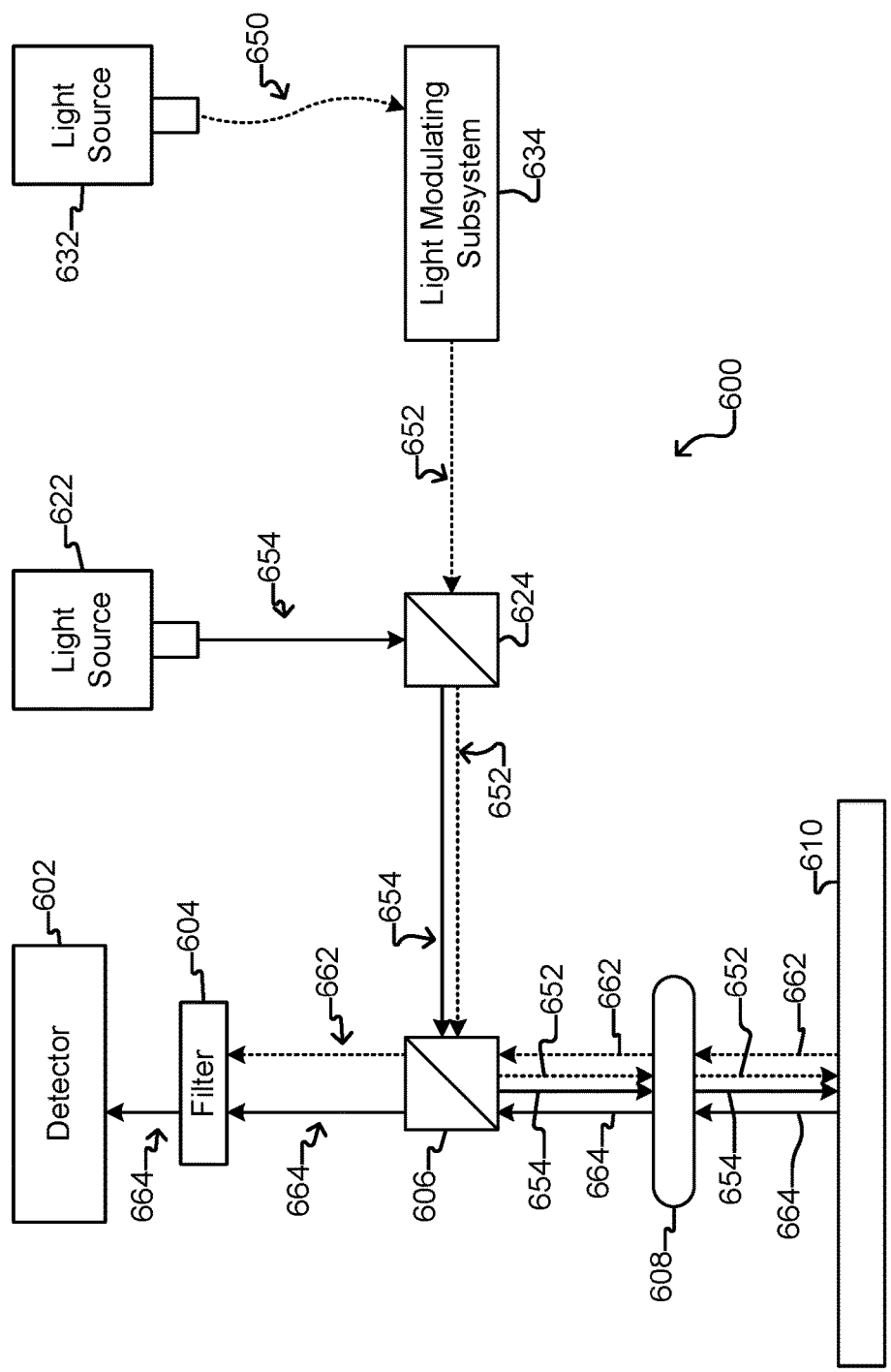

SYSTEMS FOR OPERATING ELECTROKINETIC DEVICES

RELATED APPLICATION DATA

The present application claims the benefit under 35 U.S.C. § 119 to U.S. provisional patent application Ser. Nos. 62/089,834, filed Dec. 10, 2014, and 62/259,460 filed Nov. 24, 2015. The foregoing applications are hereby incorporated by reference into the present application in their entirety.

FIELD

The present disclosure relates generally to systems for use with microfluidic devices. In particular, the present disclosure relates to systems for operating microfluidic devices.

BACKGROUND

As the field of microfluidics continues to progress, microfluidic devices have become convenient platforms for processing and manipulating micro-objects such as biological cells. Electrokinetic microfluidic devices, such as optically actuated electrokinetic microfluidic devices, offer some desirable capabilities, including the ability to select and manipulate individual micro-objects. Such microfluidic devices require various inputs (e.g., fluid, pressure, vacuum, heat, cooling, light, etc.) to function. Some embodiments of the present invention are directed to systems useful for operating electrokinetic microfluidic devices, including optically actuated electrokinetic microfluidic devices.

SUMMARY

In an exemplary embodiment of the disclosed inventions, a system for operating an electrokinetic device is provided, the system including a support configured to hold and operatively couple with an electrokinetic device, an electrical signal generation subsystem configured to apply a biasing voltage across a pair of electrodes in the electrokinetic device when the electrokinetic device is held by, and operatively coupled with, the support, and a light modulating subsystem configured to emit structured light onto the electrokinetic device when the electrokinetic device is held by, and operatively coupled with, the support. The support preferably includes a socket configured to receive and interface with the electrokinetic device. The electrical signal generation subsystem preferably includes a waveform generator configured to generate a biasing voltage waveform to be applied across the electrode pair when the electrokinetic device is held by, and operatively coupled with, the support. The electrical signal generation subsystem may further include a waveform amplification circuit configured to amplify the biasing waveform generated by the waveform generator, and/or an oscilloscope configured to measure the biasing voltage waveform, and wherein data from the measurement is provided as feedback to the waveform generator. By way of example, and without limitation, the electrokinetic device may be an optically actuated electrokinetic device.

In exemplary embodiments, the system includes a thermal control subsystem configured to regulate a temperature of the electrokinetic device when the electrokinetic device is held by, and operatively coupled with, the support. The thermal control subsystem may include a thermoelectric power module, a Peltier thermoelectric device, and a cooling unit, wherein the thermoelectric power module is configured to regulate a temperature of the Peltier thermoelectric device, and wherein the Peltier thermoelectric device is interposed between a surface of the electrokinetic device and a surface of the cooling unit. In some embodiments, the cooling unit may include a liquid cooling device, a cooling block, and a liquid path configured to circulate cooled liquid between the liquid cooling device and the cooling block, wherein the cooling block includes the surface of the cooling unit, and the respective Peltier thermoelectric device and the thermoelectric power module may be mounted on and/or integrated with the support.

In exemplary embodiments, the support includes a microprocessor that controls one or both of the electrical signal generation subsystem and the thermoelectric power module. For example, the support may include a printed circuit board (PCB), and wherein at least one of the electrical signal generation subsystem, the thermoelectric power module, and the microprocessor are mounted on and/or integrated with the PCB. The system may further include an external computational device operatively coupled with the microprocessor, wherein the external computational device includes a graphical user interface configured to receive operator input and for processing and transmitting the operator input to the microprocessor for controlling one or both of the electrical signal generation subsystem and the thermal control subsystem. For example, the microprocessor may be configured to transmit to the external computational device data and/or information sensed or received, or otherwise calculated based upon data or information sensed or received, from one or both of the electrical signal generation subsystem and the thermal control subsystem. In one such embodiment, the microprocessor and/or the external computational device are configured to measure and/or monitor an impedance of an electrical circuit across the electrodes of the electrokinetic device when the electrokinetic device is held by, and operatively coupled with, the support, wherein the microprocessor and/or the external computational device are configured to determine a flow volume of a fluid path based upon a detected change in the measured and/or monitored impedance of the electrical circuit, the fluid path including at least part of a microfluidic circuit within the electrokinetic device. The microprocessor and/or the external computational device may be additionally or alternatively configured to determine a height of an interior microfluidic chamber of the electrokinetic device based upon a detected change in the measured and/or monitored impedance of the electrical circuit, and/or be configured to determine one or more characteristics of chemical and/or biological material contained within the microfluidic circuit of the electrokinetic device based upon a detected change in the measured and/or monitored impedance of the electrical circuit.

In some embodiments, the support and/or the light modulating subsystem may be configured to be mounted on a light microscope. In other embodiments, the support and/or the light modulating subsystem are integral components of a light microscope.

In exemplary embodiments, the system includes a first fluid line having a distal end configured to be fluidically coupled to an inlet port of the electrokinetic device, and a second fluid line having a proximal end configured to be fluidically coupled to an outlet port of the electrokinetic device, respectively, when the electrokinetic device is held by, and operatively coupled with, the support, wherein the system preferably includes at least one flow controller operatively coupled with one or both of the first and second fluid lines.

In some embodiments, the system includes a first thermally-controlled flow controller operatively coupled with one of the first fluid line and the second fluid line to selectively allow fluid to flow therethrough, wherein the first thermally-controlled flow controller may include a first thermally conductive interface thermally coupled with a flow segment of the first fluid line, and at least one flow control Peltier thermoelectric device configured to controllably lower or raise a temperature of the first thermally conductive interface sufficiently to controllably freeze or thaw fluid contained in the flow segment of the first fluid line and thereby selectively prevent or allow fluid to flow through into or out of the inlet port of the electrokinetic device through the first fluid line. The first thermally-controlled flow controller may include a first housing having a first passageway through which the flow segment of the first fluid line extends, the housing further containing the first thermally conductive interface and the at least one flow control Peltier thermoelectric device; and/or insulating material at least partially surrounding the flow segment of the first fluid line proximate the first thermally conductive interface. The system may include a second thermally-controlled flow controller operatively coupled with the other one of the first fluid line and the second fluid line to selectively allow fluid to flow therethrough, wherein the second thermally-controlled flow controller may include a second thermally conductive interface thermally coupled with a flow segment of the second fluid line, and at least one flow control Peltier thermoelectric device configured to controllably lower or raise a temperature of the second thermally conductive interface sufficiently to controllably freeze or thaw fluid contained in the flow segment of the second fluid line and thereby selectively prevent or allow fluid to flow out of or into the outlet port of the electrokinetic device. The second thermally-controlled flow controller may include a second housing having a second passageway through which the flow segment of the second fluid line extends, the housing further containing the second thermally conductive interface thermally coupled with the flow segment of the second fluid line, and the at least one flow control Peltier thermoelectric device configured to controllably lower or raise a temperature of the second thermally conductive interface; and/or insulating material at least partially surrounding the flow segment of the second fluid line proximate the second thermally conductive interface.

In exemplary embodiments, the system includes a thermally-controlled flow controller operatively coupled with the first and second fluid lines, the thermally-controlled flow controller including a thermally conductive interface having a first portion thermally coupled with a flow segment of the first fluid line, and a second portion thermally coupled with a flow segment of the second fluid line, and at least one flow-control Peltier thermoelectric device configured to controllably lower or raise a temperature of the thermally conductive interface sufficiently to controllably freeze or thaw fluid contained in the respective flow segments of the first and second fluid lines and thereby selectively prevent or allow fluid to flow through the first fluid line into the inlet port of the electrokinetic device, or from the outlet port of the electrokinetic device through the outflow fluid line. In such embodiments, the at least one flow-control Peltier thermoelectric device may include a first flow-control Peltier thermoelectric device thermally coupled to the first portion of the thermally conductive interface proximate the flow segment of the first fluid line, and a second flow-control Peltier thermoelectric device thermally coupled to the second portion of the thermally conductive interface proximate the flow segment of the second fluid line. The flow controller may include a housing having a first passageway through which the flow segment of the first fluid line extends, and a second passageway through which the flow segment of the outflow fluid line extends, wherein the thermally conductive interface is mounted in the housing, for example, wherein the housing defines a thermally insulating chamber in which the thermally conductive interface is mounted.

In various embodiments, the light modulating subsystem may include one or more of a digital mirror device (DMD), a microshutter array system (MSA), a liquid crystal display (LCD), a liquid crystal on silicon device (LCOS), a ferroelectric liquid crystal on silicon device (FLCOS), and a scanning laser device.

In exemplary embodiments, the light modulating subsystem includes a multi-input structure, such as a light pipe or a crossed dichroic prism (or "x-cube"). The light pipe can include a housing having a plurality of input apertures, each input aperture configured to receive light emitted from a respective light source, the housing further having an output aperture configured to emit light received through the input apertures; a first light propagation pathway extending within the housing from a first input aperture to the output aperture; a first dichroic filter positioned within the housing at an oblique angle across the first light propagation pathway, the first dichroic filter configured and positioned so that light received through the first light aperture passes through the first dichroic filter as it propagates along the first light propagation pathway to the output aperture; and a second light propagation pathway extending within the housing from a second input aperture to the first dichroic filter, the second propagation pathway and first dichroic filter configured and dimensioned so that light received through the second input aperture propagates along the second light propagation pathway and is reflected onto the first light propagation pathway to the output aperture by the first dichroic filter, wherein the respective input apertures, first and second light propagation pathways, first dichroic filter, and output aperture are sized, dimensioned and configured such that light emitted by at least one light source and received through at least one of the first and second input apertures is emitted at substantially uniform intensity out the output aperture. The light pipe may further include a second dichroic filter positioned within the housing at an oblique angle across the first light propagation pathway between the first dichroic filter and the output aperture, the second dichroic filter configured and positioned so that light received through the first and second light apertures passes through the second dichroic filter as the received light propagates along the first light propagation pathway to the output aperture, and a third light propagation pathway extending within the housing from a third input aperture to the second dichroic filter, the third propagation pathway and second dichroic filter configured and dimensioned so that light received through the third input aperture propagates along the third light propagation pathway and is reflected onto the first light propagation pathway to the output aperture by the second dichroic filter.

The light modulating subsystem may further include a first light source having an output optically coupled with the first input aperture of the light pipe, wherein the first light source may include a plurality of first light source emitting elements, which may emit light at a first narrowband wavelength. The light modulating subsystem may further include a second light source having an output optically coupled with the second input aperture of the light pipe, for example, with the second light source including a plurality of second light source emitting elements, which may emit light at the first narrowband wavelength or at a second narrowband wavelength different from the first narrowband wavelength. The plurality of first light source emitting elements and the plurality of second light source emitting elements preferably collectively include a first subset of one or more light emitting elements that emit light at the first narrowband wavelength, and a second subset of one or more light emitting elements that emit light at a second narrowband wavelength different from the first narrowband wavelength, such that light including one or both of the first narrowband wavelength and second narrowband wavelength may be controllably emitted out the light pipe output aperture by selectively activating one or both of the plurality of first light source emitting elements and the plurality of second light source emitting elements. In this manner, light emitted by the first subset of light emitting elements and received through the first and/or second input apertures is emitted out the output aperture of the light pipe at a first substantially uniform intensity, and light emitted by the second subset of light emitting elements and received through the first and/or second input apertures is emitted out the output aperture at a second substantially uniform intensity, wherein the first substantially uniform intensity may be different from the second substantially uniform intensity.

By way of non-limiting examples, the first narrowband wave length and the second narrowband wavelength may be selected from the group consisting of approximately 380 nm, approximately 480 nm, and approximately 560 nm. In some embodiments, the plurality of light emitting elements of the first light source may include or consist of all of the first subset of light emitting elements, and the plurality of light emitting elements of the second light source may include or consist of all of the second subset of light emitting elements.

The light modulating subsystem may further include a third light source having an output optically coupled with the third input aperture of the light pipe, wherein the third light source may include a plurality of third light source emitting elements, for example, wherein one or more of the plurality of third light source emitting elements emits light at the first narrowband wavelength, the second narrowband wavelength, or a third narrowband wavelength different from each of the first and second narrowband wavelengths. In such embodiments, the plurality of first light source emitting elements, the plurality of second light source emitting elements, and the plurality of third light source emitting elements collectively including a first subset of one or more light emitting elements that emit light at the first narrowband wavelength, a second subset of one or more light emitting elements that emit light at the second narrowband wavelength different from the first narrowband wavelength, and a third subset of one or more light emitting elements that emit light at a third narrowband wavelength different from each of the first and second narrowband wavelengths, such that light including one or more of the first narrowband wavelength, second narrowband wavelength, and third narrowband wavelength may be controllably emitted out the light pipe output aperture by selectively activating one or more of the first, second and third subsets of light emitting elements. In one such embodiment, light emitted by the first subset of light emitting elements and received through any of the first, second and third input apertures is emitted out the output aperture at a first substantially uniform intensity, light emitted by the second subset of light emitting elements and received through any of the first, second and third input apertures is emitted out the output aperture at a second substantially uniform intensity, and light emitted by the third subset of light emitting elements and received through any of the first, second and third input apertures is emitted out the output aperture at a third substantially uniform intensity, wherein the first substantially uniform intensity may be different from one or both of the second substantially uniform intensity and third substantially uniform intensity. In various such embodiments, the first narrowband wave length may be approximately 380 nm, the second narrowband wavelength may be approximately 480 nm, and the third narrowband wavelength may be approximately 560 nm. In some such embodiments, the plurality of light emitting elements of the first light source may include or consist of all of the first subset of light emitting elements, the plurality of light emitting elements of the second light source may include or consist of all of the second subset of light emitting elements, and the plurality of light emitting elements of the third light source may include or consist of all of the third subset of light emitting elements.

In accordance with another aspect, embodiments of a microscope configured for operating an electrokinetic device are disclosed, wherein the microscope includes a support configured to hold and operatively couple with an electrokinetic device; a light modulating subsystem configured to emit structured light; and an optical train, wherein when the electrokinetic device is held by, and operatively coupled with, the support, the optical train is configured to: (1) focus structured light emitted by the light modulating subsystem onto at least a first region of the electrokinetic device, (2) focus unstructured light emitted by an unstructured light source onto at least a second region of the electrokinetic device, and (3) capture reflected and/or emitted light from the electrokinetic device and direct the captured light to a detector. In preferred embodiments, the microscope also includes the detector, which may be an eye piece and/or an imaging device. The light modulating subsystem may include one or more of a digital mirror device (DMD) or a microshutter array system (MSA), a liquid crystal display (LCD), a liquid crystal on silicon device (LCOS), a ferroelectric liquid crystal on silicon device (FLCOS), and a scanning laser device, wherein the microscope preferably includes a controller for controlling the light modulating subsystem. The optical train may include an objective which is configured to focus the structured light on the first region of the microfluidic device and/or the unstructured light on the second region of the microfluidic device, and wherein the objective is selected from the group including: a 10× objective; a 5× objective; a 4× objective; and a 2× objective.

In some embodiments, the optical train includes a dichroic filter configured to substantially prevent structured light emitted by the light modulating subsystem (and reflected by the electrokinetic device) from reaching the detector.

In some embodiments, the optical train includes a dichroic filter configured to balance an amount of visible structured light emitted by the light modulating subsystem (and reflected by the electrokinetic device) and an amount of visible unstructured light emitted by the unstructured light source (and reflected by the electrokinetic device) that reaches the detector.

In some embodiments, the light modulating subsystem emits structured white light.

In some embodiments, the light modulating subsystem includes one or more of a Mercury, a Xenon arc lamp, and one or more LEDs. In certain embodiments, the light modulating subsystem includes a multi-input structure, such as a light pipe or a crossed dichroic prism (or "x-cube").

In some embodiments, the unstructured light source includes one or more LEDs, for example, wherein the unstructured light source emits light having a wavelength of approximately 495 nm or shorter (e.g., blue light), wherein the optical train preferably includes a dichroic filter configured to at least partially filter out visible light having a wavelength longer than 495 nm.

In some embodiments, the unstructured light source includes one or more LEDs, for example, wherein the unstructured light source emits light having a wavelength of approximately 650 nm or shorter (e.g., red light), wherein the optical train preferably includes a dichroic filter configured to at least partially filter out visible light having a wavelength shorter than 650 nm.

In exemplary embodiments, the microscope support includes one or both of an integrated electrical signal generation subsystem configured to apply a biasing voltage across a pair of electrodes in the electrokinetic device, and a thermal control subsystem configured to regulate a temperature of the electrokinetic device, respectively, when the device is held by, and operatively coupled with, the support, the support. By way of example, and without limitation, the electrokinetic device may be an optically actuated electrokinetic device.

In accordance with yet another aspect, embodiments of a multi-input light pipe are disclosed. In an exemplary embodiment, the light pipe includes a light pipe housing having a plurality of input apertures, each input aperture configured to receive light emitted from a respective light source, the housing further having an output aperture configured to emit light received through the input apertures; a first light propagation pathway extending within the housing from a first input aperture to the output aperture; a first dichroic filter positioned within the housing at an oblique angle across the first light propagation pathway, the first dichroic filter configured and positioned so that light received through the first light aperture passes through the first dichroic filter as it propagates along the first light propagation pathway to the output aperture; and a second light propagation pathway extending within the housing from a second input aperture to the first dichroic filter, the second propagation pathway and first dichroic filter configured and dimensioned so that light received through the second input aperture propagates along the second light propagation pathway and is reflected onto the first light propagation pathway to the output aperture by the first dichroic filter, wherein the respective input apertures, first and second light propagation pathways, first dichroic filter, and output aperture are sized, dimensioned and configured such that light emitted by at least one light source and received through at least one of the first and second input apertures is emitted at substantially uniform intensity out the output aperture. The light pipe may also include a second dichroic filter positioned within the housing at an oblique angle across the first light propagation pathway between the first dichroic filter and the output aperture, the second dichroic filter configured and positioned so that light received through the first and second light apertures passes through the second dichroic filter as the received light propagates along the first light propagation pathway to the output aperture, and a third light propagation pathway extending within the housing from a third input aperture to the second dichroic filter, the third propagation pathway and second dichroic filter configured and dimensioned so that light received through the third input aperture propagates along the third light propagation pathway and is reflected onto the first light propagation pathway to the output aperture by the second dichroic filter.

In accordance with still another aspect, embodiments of a light transmission system are disclosed, including the above-summarized light pipe and at least a first light source having an output optically coupled with the first input aperture of the light pipe. By way of example, the first light source may include a plurality of first light source emitting elements, wherein one or more first light source emitting elements may emit light at a first narrowband wavelength. The light transmission system may include a second light source having an output optically coupled with the second input aperture of the light pipe. By way of example, the second light source may include a plurality of second light source emitting elements, wherein the second light source emitting elements may emit light at the first narrowband wavelength or at a second narrowband wavelength different from the first narrowband wavelength.

In one such embodiment, the plurality of first light source emitting elements and the plurality of second light source emitting elements collectively include a first subset of one or more light emitting elements that emit light at the first narrowband wavelength, and a second subset of one or more light emitting elements that emit light at a second narrowband wavelength different from the first narrowband wavelength, such that light including one or both of the first narrowband wavelength and second narrowband wavelength may be controllably emitted out the light pipe output aperture by selectively activating one or both of the first and second subsets of light emitting elements. In such embodiment, light emitted by the first subset of light emitting elements and received through the first and/or second input apertures may be emitted out the output aperture of the light pipe at a first substantially uniform intensity, and light emitted by the second subset of light emitting elements and received through the first and/or second input apertures is emitted out the output aperture at a second substantially uniform intensity, which may or may not be different from the first substantially uniform intensity. By way of non-limiting examples, the first narrowband wave length and the second narrowband wavelength may be selected from the group consisting of approximately 380 nm, approximately 480 nm, and approximately 560 nm. In some embodiments, the plurality of light emitting elements of the first light source may include or consist of all of the first subset of light emitting elements, and the plurality of light emitting elements of the second light source may include or consist of all of the second subset of light emitting elements.

The light transmission system may further include a third light source having an output optically coupled with the third input aperture of the light pipe, wherein the third light source may include a plurality of third light source emitting elements in which one or more of the plurality of third light source emitting elements emits light at the first narrowband wavelength, the second narrowband wavelength, or a third narrowband wavelength different from each of the first and second narrowband wavelengths. In one such embodiment of the light transmission system the plurality of first light source emitting elements, the plurality of second light source emitting elements, and the plurality of third light source emitting elements collectively include a first subset of one or more light emitting elements that emit light at a first narrowband wavelength, a second subset of one or more light emitting elements that emit light at a second narrowband wavelength different from the first narrowband wavelength, and a third subset of one or more light emitting elements that emit light at a third narrowband wavelength different from each of the first and second narrowband wavelengths, such that light including one or more of the first narrowband wavelength, second narrowband wavelength, and third narrowband wavelength may be controllably emitted out the light pipe output aperture by selectively activating one or more of the first, second and third subsets of light emitting elements. In this manner, light emitted by the first subset of light emitting elements and received through any of the first, second and third input apertures is emitted out the output aperture at a first substantially uniform intensity, light emitted by the second subset of light emitting elements and received through any of the first, second and third input apertures is emitted out the output aperture at a second substantially uniform intensity, and light emitted by the third subset of light emitting elements and received through any of the first, second and third input apertures is emitted out the output aperture at a third substantially uniform intensity, wherein the first substantially uniform intensity may or may not be different from one or both of the second substantially uniform intensity and third substantially uniform intensity. The plurality of light emitting elements of the first light source may include or consist of all of the first subset of light emitting elements, the plurality of light emitting elements of the second light source may include or consist of all of the second subset of light emitting elements, and the plurality of light emitting elements of the third light source may include or consist of all of the third subset of light emitting elements.

BRIEF DESCRIPTION OF THE DRAWINGS

The drawings illustrate the design and utility of embodiments of the disclosed invention, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed invention and are not therefore to be considered limiting of its scope.

FIG. 1A is a perspective view of a support, configured to hold an electrokinetic microfluidic device, according to some embodiments of the invention.

FIG. 6 is a schematic view of a system for operating an electrokinetic microfluidic device, according to some embodiments of the invention. The system depicted in FIG. 6 includes an optical train having various beam-splitters and/or dichroic filters, a first light source, a second light source, a light modulating subsystem, an objective, and a detector.

FIG. 8A illustrates how the light intensity measured at the sample plane can vary across a field of view. FIG. 8B illustrates an inverted function that can be used to control the light intensity output from a light modulating subsystem. FIG. 8C illustrates the light intensity measured at the sample plane when the inverted function, such as shown in FIG. 8B, is used to control the light intensity output from a light source that would otherwise produce the pattern of light intensity shown in FIG. 8A.

DETAILED DESCRIPTION OF EXEMPLARY EMBODIMENTS

Figure 1B:
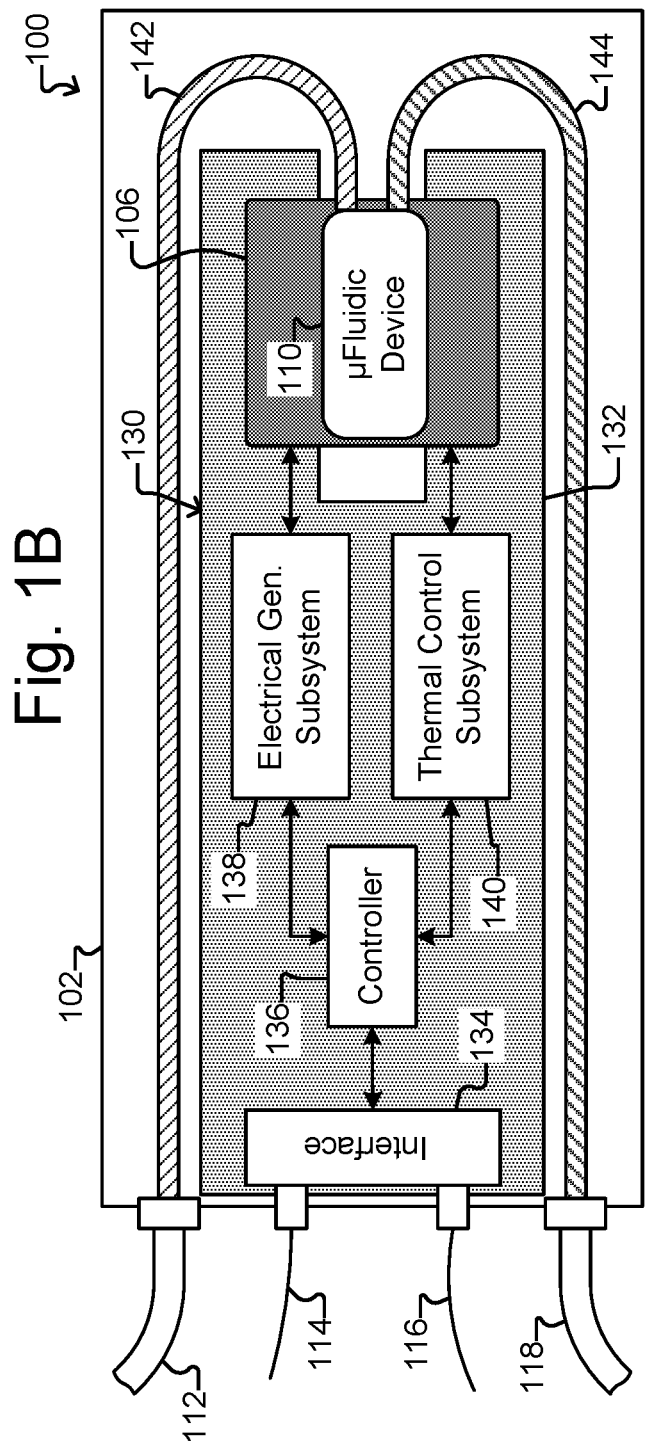
FIG. 1B is a schematic view of the support shown in FIG. 1A, with the cover removed for clarity.

This specification describes exemplary embodiments and applications of the invention. The invention, however, is not limited to these exemplary embodiments and applications or to the manner in which the exemplary embodiments and applications operate or are described herein. Further, the figures may show simplified or partial views, and the dimensions of elements in the figures may be exaggerated or otherwise not in proportion. Moreover, elements of similar structures or functions are represented by like reference numerals throughout the figures. In addition, an illustrated embodiment needs not have all the aspects or advantages shown. An aspect or an advantage described in conjunction with a particular embodiment is not necessarily limited to that embodiment, and can be practiced in any other embodiments even if not so illustrated.

For the following defined terms, these definitions shall be applied, unless a different definition is given in the claims or elsewhere in this specification.

As the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent. The term "ones" means more than one.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used herein, the term "disposed" encompasses within its meaning "located."

As used herein, the singular forms "a", "an", and "the" include plural referents unless the content clearly dictates otherwise. As used herein, the term "or" is generally employed in its sense including "and/or" unless the content clearly dictates otherwise.

In some embodiments, a system of the invention can include a support (also known as a "nest") configured to hold an electrokinetic device and a light modulating subsystem configured to receive unstructured light and emit structured light.

The support can include, for example, a socket configured to interface with and/or hold an optically actuated electrokinetic device, a printed circuit board assembly (PCBA), an electrical signal generation subsystem, a thermal control subsystem, or any combination thereof.

In certain embodiments of the invention, the support includes a socket capable of interfacing with an electrokinetic device, such as an optically actuated electrokinetic device. An exemplary socket 106 is included in the support 100 of FIGS. 1A and 1B. However, the shape and functionality of the socket 106 need not be exactly as shown in FIGS. 1A and 1B. Rather, it can be adjusted as needed to match the size and type of electrokinetic device 110 with which the socket 106 is intended to interface. A variety of electrokinetic devices 110 are known in the art, including devices 110 having optically actuated configurations, such as an optoelectronic tweezer (OET) configuration and/or an opto-electrowetting (OEW) configuration. Examples of suitable OET configurations are illustrated in the following U.S. patent documents, each of which is incorporated herein by reference in its entirety, as though set forth in full: U.S. Pat. No. RE44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and US Patent Application Publication No. 2012/0024708 (Chiou et al.), both of which are incorporated by reference herein in their entirety, as though set forth in full. Yet another example of optically actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety, as though set forth in full.

The support 100 depicted in FIGS. 1A and 1B also includes a base 102 and a cover 104 (omitted in FIG. 1B). The support 100 also includes a plurality of connectors: a first fluidic input/output 112; a communications connection 114; a power connection 116; and a second fluidic input/output 118. The first and second fluidic input/outputs 112, 118 are configured to deliver a cooling fluid to and from a cooling block (shown in FIG. 3) used to cool the electrokinetic device 110. Whether the first and second fluidic input/outputs 112, 118 are input or outputs depends on the direction of fluid flow through the support 100. The first and second fluidic input/outputs 112, 118 are fluidly coupled to the cooling block by first and second fluidic connectors 142, 144 disposed in the support 100. The communications connection 114 is configured to connect the support 110 with other components of the system for operating electrokinetic microfluidic devices, as described below. The power connection 116 is configured to provide power (e.g., electricity) to the support 110.

In certain embodiments, the support 100 can include an integrated electrical generation subsystem 138. The electrical generation subsystem 138 can be configured to apply a biasing voltage across a pair of electrodes in an electrokinetic device 110 that is being held by the support 100. The ability to apply such a biasing voltage does not mean that a biasing voltage will be applied at all times when the electrokinetic device 110 is held by the support 100. Rather, in most cases, the biasing voltage will be applied intermittently, e.g., only as needed to facilitate the generation of electrokinetic forces, such as dielectrophoresis or electrowetting, or the measurement of complex impedance in the electrokinetic device 110.

Figure 2:
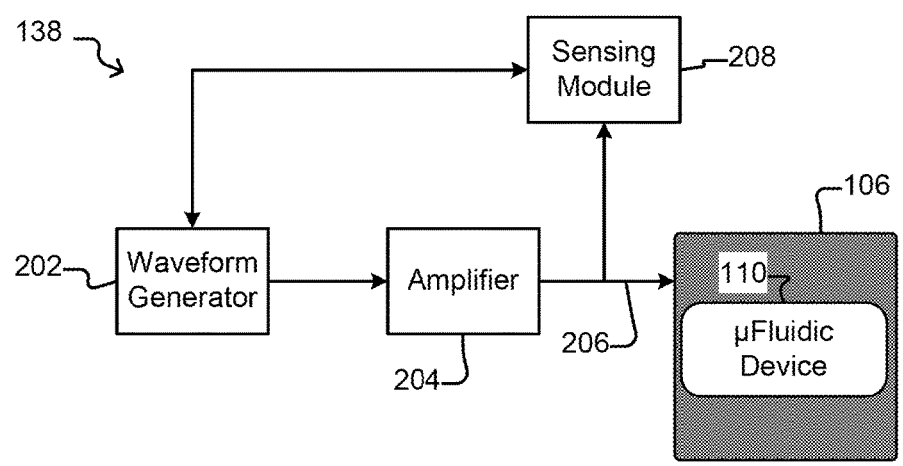
FIG. 2 is a schematic view of elements of an electrical signal generation subsystem, according to some embodiments of the invention.

Typically, the electrical signal generation subsystem 138 will include a waveform generator 202, as shown in FIG. 2. The electrical generation subsystem 138 can further include a sensing module 208 (e.g., an oscilloscope) and/or a waveform amplification circuit 204 configured to amplify a waveform received from the waveform generator 202. The sensing module 208, if present, can be configured to measure the waveform supplied to the electrokinetic device 110 held by the support 100. In certain embodiments, the sensing module 208 measures the waveform at a location proximal to the electrokinetic device 110 (and distal to the waveform generator 202), thus ensuring greater accuracy in measuring the waveform actually applied to the electrokinetic device 110. Data obtained from the sensing module 208 measurement can be, for example, provided as feedback to the waveform generator 202, and the waveform generator 202 can be configured to adjust its output based on such feedback. An example of a suitable combined waveform generator 202 and sensing module 208 is the RED PITAYA™.

Figure 3:
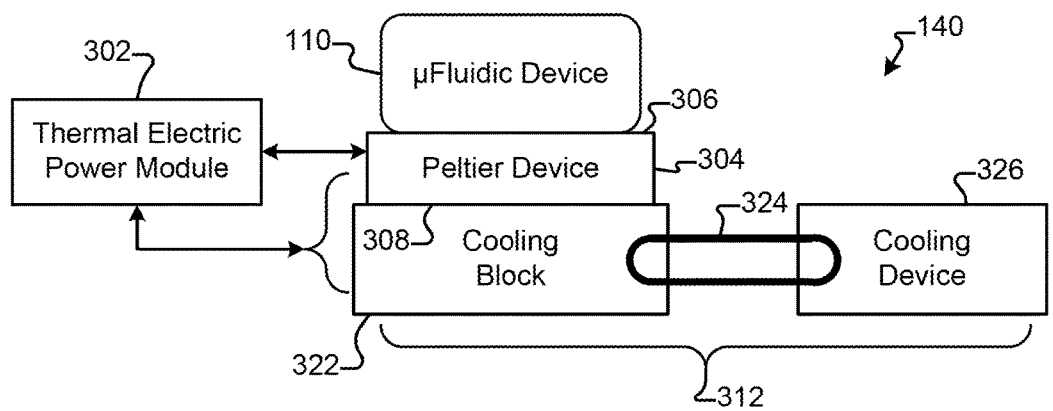
FIG. 3 is a schematic view of a thermal control subsystem, according to some embodiments of the invention.

In certain embodiments, the support 100 can include a thermal control subsystem 140. The thermal control subsystem 140 can be configured to regulate the temperature of an electrokinetic device 110 held by the support 100. As shown in FIG. 3, the thermal control subsystem 140 can include a Peltier thermoelectric device 304 and a proximal component of a cooling unit 312. The Peltier thermoelectric device 304 can have a first surface 306 configured to interface with at least one surface of the electrokinetic device 110. The cooling unit can include, for example, a cooling block 322. A second surface 308 of the Peltier thermoelectric device 304 (e.g., a surface 308 opposite the first surface 306) can be configured to interface with a surface of such a cooling block 322. All or part of the cooling block 322 (e.g., a part that interfaces with the Peltier thermoelectric device 304) can be made from a material having a high thermal conductivity. For example, the material can be a metal, such as aluminum. The cooling block 322 can be connected to a fluidic path 324 configured to circulate cooled fluid between a fluidic cooling device 326 and the cooling block 322. The fluidic path 324 can include the fluidic input/outputs 112, 118 and the fluidic connectors 142, 144 described in connection with FIG. 1. The Peltier thermoelectric device 304 and the cooling block 322 can be mounted on the support 100.

Figure 4:
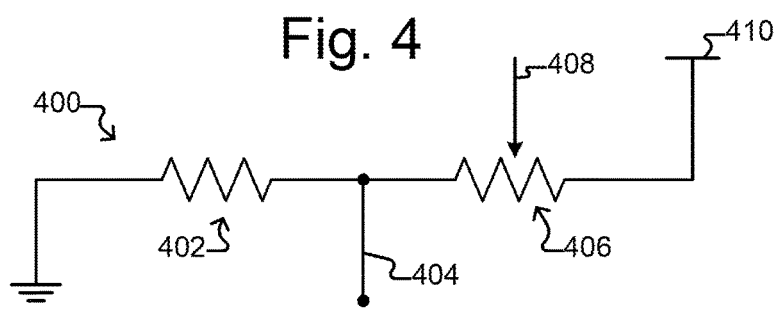
FIG. 4 is a circuit diagram depicting an analog circuit used for thermal control feedback in a thermal control subsystem, according to some embodiments of the invention.

The thermal control subsystem 140 can further include a thermoelectric power module 302, as shown in FIG. 3. The thermoelectric power module 302 can regulate the temperature of the Peltier thermoelectric device 304 so as to achieve a target temperature for the microfluidic device 110. Feedback for the thermoelectric power module 302 can include a temperature value provided by an analog circuit 400, such as shown in FIG. 4. Alternatively, the feedback can be provided by a digital circuit (not shown). The Peltier thermoelectric device 304, the cooling block 322, and the thermoelectric power module 302 all can be mounted on the support 100.

In certain embodiments, the support 100 can also include or interface with an environmental temperature monitor/regulator in addition to the thermal control subsystem 140.

The analog circuit 400 depicted in FIG. 4 includes a resistor 402, a thermistor 406, and an analog input 404. The analog input is operatively coupled to the electrical signal generation subsystem 138 (e.g., the sensing module 208 thereof) and provides a signal thereto that can be used to calculate the temperature of the electrokinetic device 110. The thermistor 406 is configured such that its resistance may decrease in a known manner when the temperature of the thermistor 406 decreases and increase in a known manner when the temperature of the thermistor 406 increases. The analog circuit 400 is connected to a power source 410 which is configured to deliver a biasing voltage to electrode 408. In one particular embodiment, the resistor 402 can have a resistance of about 10,000 ohms, the thermistor 406 can have a resistance of about 10,000 ohms at 25° C., and the power source 410 (e.g., a DC power source) can supply a biasing voltage of about 5 V. The analog circuit 400 is exemplary, and other systems can be used to provide a temperature value for feedback for the thermoelectric power module 302.

Figure 5:
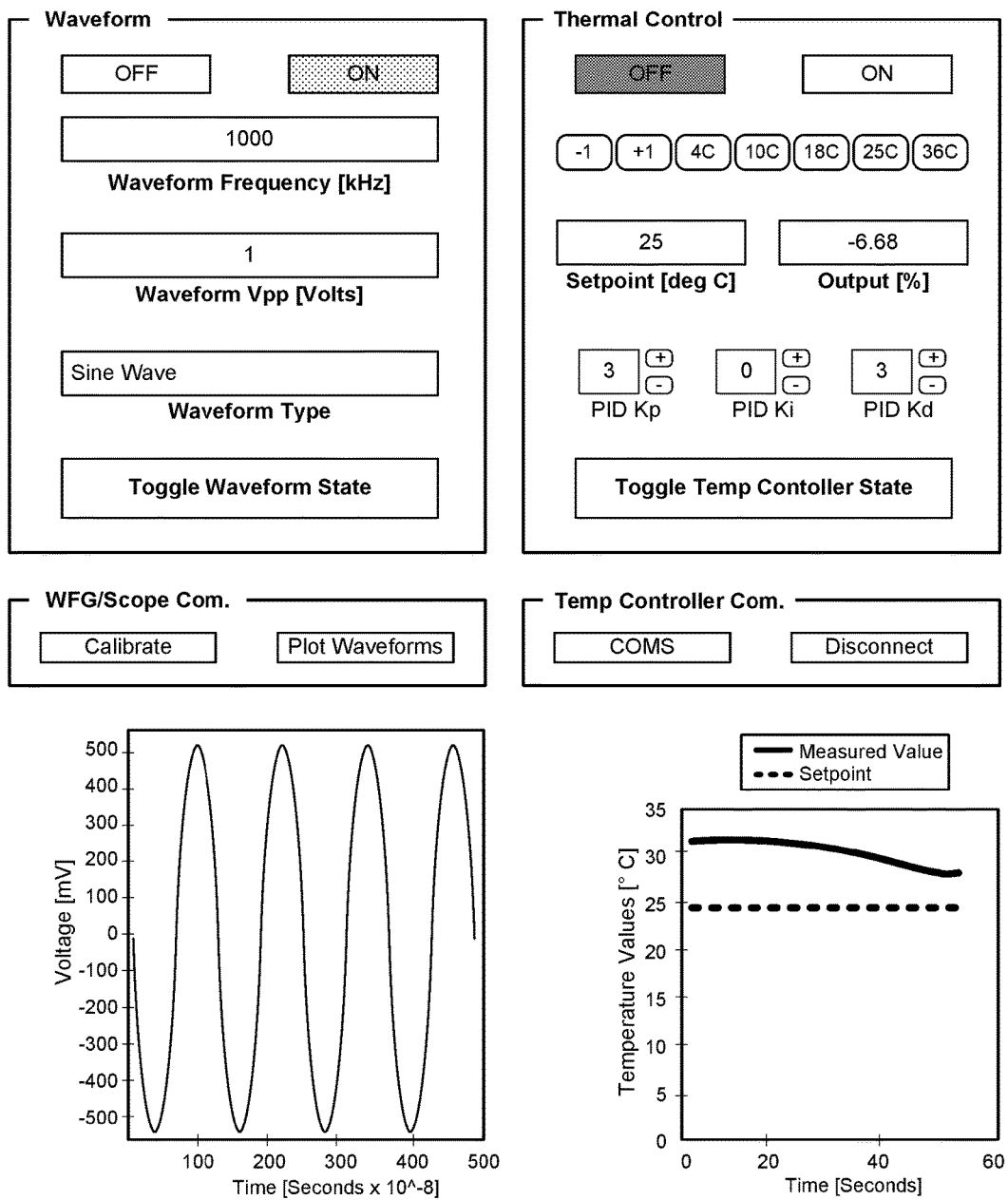
FIG. 5 is an exemplary screen shot depicting a graphical user interface (GUI) used to control both an electrical signal generation subsystem and a thermal control subsystem, according to some embodiments of the invention.

In certain embodiments, the support 100 further comprises a controller 136 (e.g., a microprocessor). The controller 136 can be used to sense and/or control the electrical signal generation subsystem 138. In addition, to the extent that the support 100 includes a thermal control subsystem 140, the controller 136 can be used to sense and/or control the thermal control subsystem 140. Examples of suitable controllers 136 include the ARDUINO™ microprocessors, such as the ARDUINO NANO™. The controller 136 can be configured to interface with an external controller (not shown), such as a computer or other computational device, via a plug/connector 134. In certain embodiments, the external controller can include a graphical user interface (GUI) configured to sense and/or control the electrical signal generation subsystem 138, the thermal control subsystem 140, or both. An exemplary GUI 500, which is configured to control both the electrical signal generation subsystem 138 and the thermal control subsystem 140, is depicted in FIG. 5.

In certain embodiments, the support 100 can include a printed circuit board (PCB) 132. The electrical signal generation subsystem 138 can be mounted on and electrically integrated into the PCB 132. Similarly, to the extent that the support 100 includes a controller 136 or a thermal control subsystem 140, the controller 136 and/or the thermoelectric power module 302 can be mounted on and electrically integrated into the PCB 132.

Thus, as shown in FIGS. 1A and 1B, an exemplary support 100 can include a socket 106, an interface 134, a controller 136, an electrical signal generation subsystem 138, and a thermal control subsystem 140, all of which are mounted on and electrically integrated into PCB 132, thereby forming a printed circuit board assembly (PCBA) 130. As discussed above, the socket 106 can be designed to hold an electrokinetic device 110 (or "consumable"), including an optically actuated electrokinetic device.

In certain specific embodiments, the electrical generation subsystem 138 can include a RED PITAYATM™ waveform generator 202/sensing module 208 and a waveform amplification circuit 204 that amplifies the waveform generated by the RED PITAYATM waveform generator 202 and passes the amplified waveform (voltage) 206 to the electrokinetic device 110. Both the RED PITAYATM™ unit 202, 208 and the waveform amplification circuit 204 can be electrically integrated into the PCB 132 as an electrical signal generation subsystem 138, as shown in FIG. 1B. Moreover, the RED PITAYATM™ unit 202, 208 can be configured to measure the amplified voltage at the electrokinetic device 110 and then adjust its own output voltage as needed such that the measured voltage at the electrokinetic device 110 is the desired value. The amplification circuit 204 can have, for example, a +6.5V to −6.5V power supply generated by a pair of DC-DC converters mounted on the PCB 132, resulting in a signal of up to 13 Vpp at the electrokinetic device 110.

In certain specific embodiments, the support 100 includes a thermal control subsystem 140 (shown in FIG. 3) having a Peltier thermoelectric device 304, located between a liquid-cooled aluminum block 322 and the back side of the electrokinetic device 110, a POLOLU™ thermoelectric power supply (not shown), and an ARDUINO NANO™ controller 136. Feedback for the thermal control subsystem 140 can be an analog voltage divider circuit 400 (shown in FIG. 4) which includes a resistor 402 (e.g. resistance 10 kOhm+/−0.1%, temperature coefficient +/−0.02 ppm/C.°)

and a negative temperature coefficient thermistor 406 (nominal resistance 10 kOhm+/−0.01%). The controller 136 can measure the voltage from the feedback circuit 400 and then use the calculated temperature value as input (e.g., to an on-board PID control loop algorithm) to drive both a directional and a pulse-width-modulated signal pin on the thermoelectric power module 302, and thereby actuate the thermoelectric subsystem 140. A liquid cooling unit 326 can be configured to pump fluid through the cooling path 324 located, in part, in the support 100 (e.g., fluidic input/outputs 112, 118 and the fluidic connectors 142, 144) and, in part, at the periphery of the support 100.

In certain specific embodiments, the support 100 includes a serial port 114 and a Plink tool that together allow the RED PITAYA™ unit to communicate with an external computer. The serial port 114 can also allow the controller 136 to communicate with the external computer. Alternatively, a separate serial port (not shown) can be used to allow the controller 136 to communicate with the external computer. In other embodiments, the support 100 can include a wireless communication device configured to facilitate wireless communication between components of the support 100 (e.g., the controller 136 and/or the electrical generation subsystem 138) and the external computer, which can include a portable computing device such as a cell phone, a PDA, or other handheld device. A GUI (e.g., such as shown in FIG. 5) on the external computer can be configured for various functions, including, but not limited to, plotting temperature and waveform data, performing scaling calculations for output voltage adjustment, and updating the controller 136 and RED PITAYA™ device 202, 208.

In certain embodiments, the support 100 can also include or interface with an inductance/capacitance/resistance (LCR) meter configured to measure characteristics of the contents (e.g., fluidic contents) of the electrokinetic device 110.

For example, the LCR meter can be configured to measure the complex impedance of a system, particularly the complex impedance of a fluid as it enters, is located within, and/or as it exits an electrokinetic device 110. In some embodiments, the LCR meter can be connected to and/or integrated into a fluid line that carries fluid into or out of the electrokinetic device 110. In other embodiments, the LCR meter can be connected to or an integral part of the electrical generation subsystem 138. Thus, in certain specific embodiments, the RED PITAYA™ waveform generator 202 and sensing module 208 in the support 100 can be configured to function as an LCR meter. In certain embodiments, electrodes of the electrokinetic device 110 which are configured for use with the electrical generation subsystem 138 can also be configured for use with the LCR meter. Measuring the impedance of a system can determine various system characteristics and changes therein, such as the height of the fluidic circuit within the electrokinetic device 110, changes in the salt content of fluid in the electrokinetic device 110 (which may correlate with the status of biological micro-objects therein), and the movement of specific volumes of fluids (having different impedances) through the electrokinetic device 110.

Figure 9:
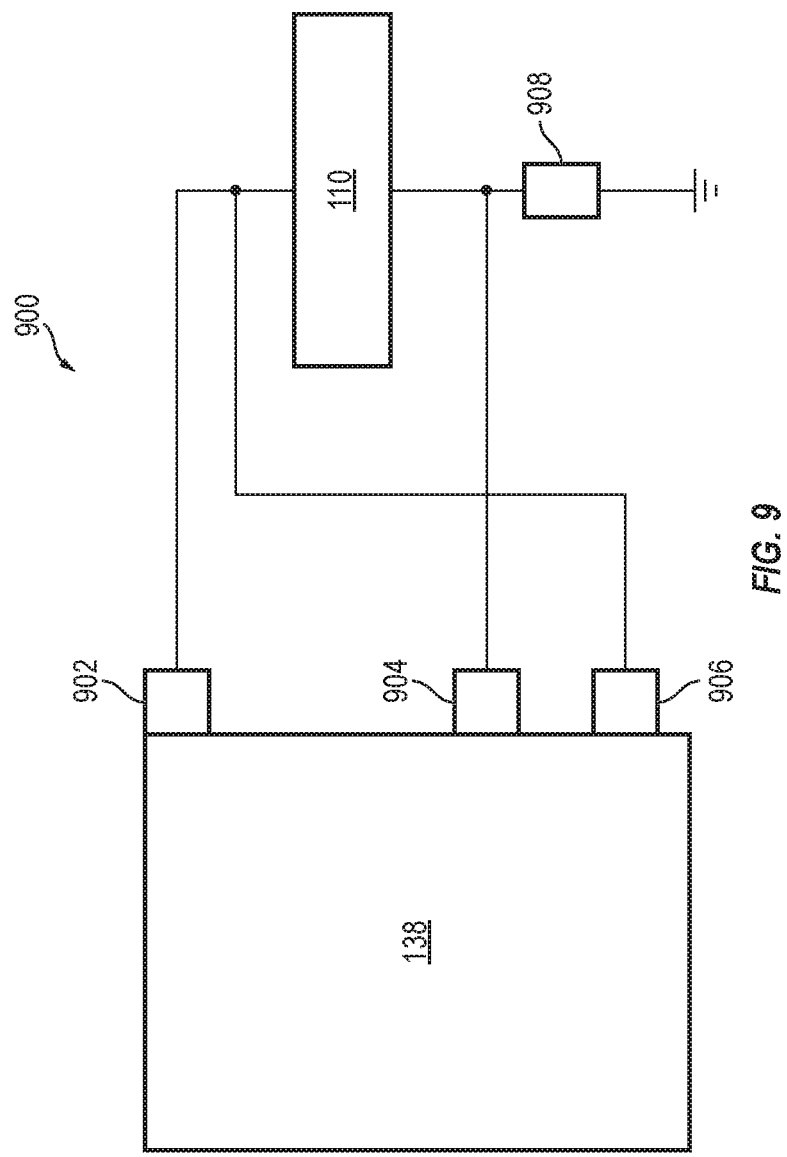
FIG. 9 is a schematic view of an impedance measurement circuit, according to some embodiments of the invention.

In certain embodiments, measuring the impedance of a system can be used to accurately (i.e., close to the true value) and precisely (i.e., repeatably) detect a change from a first fluid in a system (i.e., the electrokinetic device 110) to a second fluid in the system. For example, the first fluid could be deionized water (DI) and the second fluid could be a saline solution (e.g., phosphate-buffered saline or "PBS"), or vice versa. Alternatively, the first fluid could be a saline solution (e.g., PBS) and the second fluid could be a cell culture medium having an impedance that is detectably different than the saline solution, or vice versa. In still other alternatives, the first fluid could be a first cell culture medium and the second fluid could be a second cell culture medium having an impedance that is detectably different than the first cell culture medium. FIG. 9 is a diagram depicting an impedance measurement circuit 900 for detecting the impedance of a system. The circuit 900 includes an output 902 from the waveform generator 202 of the electrical generation subsystem 138, and two inputs 904, 906 to the sensing module 208 of the electrical generation subsystem 138. The circuit 900 also includes the electrokinetic device 110 (connected via the socket 106 of the support 100) and a shunt resistor 908. The shunt resistor 908 can be selected so as to render the LCR sufficiently accurate to measure impedances in the 0 to about 5,000 ohm range (e.g., 0 to about 4,000, 0 to about 3,000, 0 to about 2,500, 0 to about 2,000, 0 to about 1,500, or 0 to about 1,000 ohm range). The electrokinetic device 110 functions in the circuit 900 as a measurement cell, with the base (e.g., a semi-conductor device) and cover (e.g., having an indium tin oxide (ITO) layer) of the electrokinetic device 110 functioning as electrodes. In certain specific embodiments, the output 902 of circuit 900 can come from the waveform generator 202 of a RED PITAYA™ device and the inputs 904, 906 can originate from the electrokinetic device 110 and be received by the sensing module 208 of the RED PITAYA™ device. In certain specific embodiments, the shunt resistor 908 can be a 50 ohm resistor. In these embodiments, the electrical generation subsystem 138 may be switched between an "optical actuation mode" and an "LCR mode." Moreover, when in LCR mode, the electrical generation subsystem 138 can be connected to a computer running a MATLAB script.

The system of the invention thus provides methods for determining the flow volume ($V_{flow}$) of an electrokinetic device 110. For example, the electrokinetic device 110 is initially filled with a first fluid associated with a first impedance (e.g., DI, which is associated with an impedance of about 450 ohms). Then, a second fluid associated with a second impedance that is detectably different than the first impedance (e.g., PBS, which is associated with an impedance of about 160 ohms) is flowed into and through the electrokinetic device 110. The second fluid can be flowed into the electrokinetic device 110, for example, through a port capable of functioning as either a fluid inlet port or a fluid outlet port. The system continuously measures the complex impedance of the electrokinetic device 110 as the second fluid is flowing into and through the electrokinetic device 110. As discussed above, to measure the complex impedance of the electrokinetic device 110 at a particular time point, the system applies a voltage potential to the electrokinetic device 110 and, concomitantly, receives signals from the electrokinetic device 110 that are used to calculate the complex impedance. The voltage potential applied to the electrokinetic device can have a frequency of about 10 kHz to about 1 MHz (e.g., about 50 kHz to about 800 kHz, about 100 kHz to about 700 kHz, about 200 kHz to about 600 kHz, about 300 kHz to about 500 kHz, about 350 kHz to about 400 kHz, or about 380 kHz). The specific frequency can be selected based on properties of the electrokinetic device 110 and the first and second fluids so as to optimize accuracy of the impedance measurement, minimize measurement time, and reduce inductive effects. The second fluid is flowed into and through the electrokinetic device 110 until the measured complex impedance changes from the first impedance associated with the first fluid to the second impedance associated with the second fluid. The minimum amount of second fluid required to completely switch the complex impedance of the electrokinetic device 110 from the first impedance to the second impedance is a measure of the flow volume ($V_{flow}$) of the electrokinetic device. Starting from the point when the system begins to pump the second fluid to the electrokinetic device 110, the volume of the second fluid required to switch the complex impedance of the electrokinetic device 110 from the first impedance to the second impedance can include (1) the flow volume ($V_{flow}$) of the electrokinetic device 110, (2) the volume of the fluid outlet port of the electrokinetic device, and (3) the flow volume of the tubing carrying the second fluid from a pump to the electrokinetic device 110. Because the flow of the second fluid through the tubing and fluid outlet port does not change the complex impedance of the electrokinetic device 110, the flow volume of the tubing and inlet port can be readily distinguished from the flow volume of the electrokinetic device 110.

Using the calculated flow volume of an electrokinetic device 110, the system further provides methods for reliably exporting one or more micro-objects from the electrokinetic device 110 in a discrete volume of fluid. Having determined the flow volume ($V_{flow}$) of the electrokinetic device 110, the minimal export volume ($V_{ex}$) needed to export a micro-object (e.g., a biological cell) positioned within the flow path can be approximated by calculating the portion of the flow path that separates the micro-object from the fluid outlet port of the electrokinetic device 110. For example, a total length ($L_{tot}$) of the flow path can be determined by tracing the flow path of the electrokinetic device 110 from the fluid inlet port to the fluid outlet port. The export length ($L_{ex}$) of the flow path can be determined by tracing the flow path of the electrokinetic device 110 from the location of the micro-object in the flow path to the fluid output port. The minimal amount of fluid ($V_{ex}$) needed to export the micro-object from the electrokinetic device 110 can thus be calculated as: $V_{ex}=(L_{ex}/L_{tot})*V_{flow}$. Alternatively, the total volume of the flow path ($V_{flow-tot}$) can be estimated from the predicted geometry of the flow path (e.g., using CAD drawings); and the total volume of the export flow path ($V_{ex-tot}$) can likewise be calculated from the predicted geometry of the flow path. In such an embodiment, minimal amount of fluid ($V_{ex}$) need to export the micro-object from the electrokinetic device 110 can be calculated as: $V_{ex}=(V_{ex-tot}/V_{flow-tot})*V_{flow}$. Regardless of the approach to calculating $V_{ex}$, the micro-object can be exported from the electrokinetic device 110 by flowing a volume of fluid through the fluid outlet port of the electrokinetic device 110 that is at least as large as $V_{ex}$. To ensure reliable export, the micro-object can be exported from the electrokinetic device 110 by flowing a volume of fluid ($V_{ex-rel}$) that is equal to C*Vex, wherein C is a scaling factor that is equal to about 1.1 or greater (e.g., about 1.2, 1.3, 1.4, 1.5, 1.6, 1.7, 1.8, 1.9, 2.0, or greater). In some methods, a leading portion of $V_{ex}$ (or $V_{ex-rel}$) is discarded before a residual volume ($V_{res}$, equal to $V_{ex}$ (or $V_{ex-rel}$) minus the leading portion) that contains the micro-object(s) is exported from the electrokinetic device 110. For example, $V_{ex}$ (or $V_{ex-rel}$) could equal 1.0 μL and a leading volume of 0.5 μL could be discarded, resulting in the micro-object(s) being exported in a final volume $V_{res}$ of 0.5 μL. In this manner, the micro-object(s) can be exported in a small but discrete volume of fluid. Depending on how the method is performed, $V_{ex}$, $V_{ex-rel}$, or $V_{res}$ can be about 2.0 μL, 1.5 μL, 1.2 μL, 1.0 μL, 0.9 μL, 0.8 μL, 0.7 μL, 0.6 μL, 0.5 μL, 0.4 μL, 0.3 μL, 0.25 μL, or less. Typically, the volume of fluid containing the micro-object(s) (i.e., $V_{ex}$, $V_{ex-rel}$, or $V_{res}$) is exported through export tubing having a finite internal volume before reaching a collection receptacle. Accordingly, the calculations used in the methods can be adjusted to account for the known or estimated volume of the export tubing. For example, the export tubing could have an internal volume of 5.0 μL. In such a case, a $V_{ex}$ (or $V_{ex-rel}$) of 1.0 μL would be adjusted to 6.0 μL, and a discarded leading volume of 0.5 μL would be adjusted to 5.5 μL, thus resulting in a $V_{res}$ of 0.5 μL remaining the same.

Figure 10:
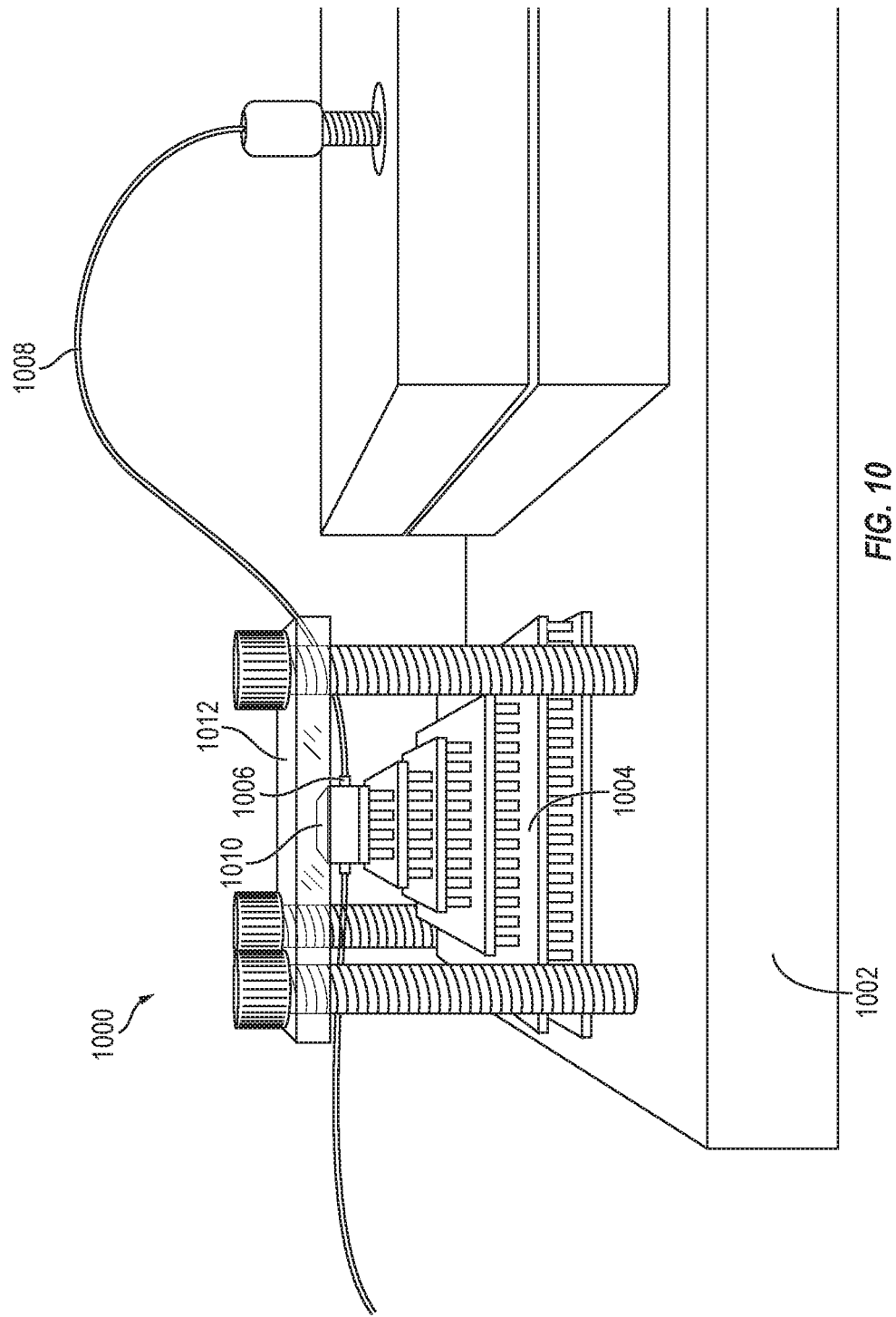
FIGS. 10 and 11 are side and perspective views of a freeze valve, according to some embodiments of the invention.
Figure 11:
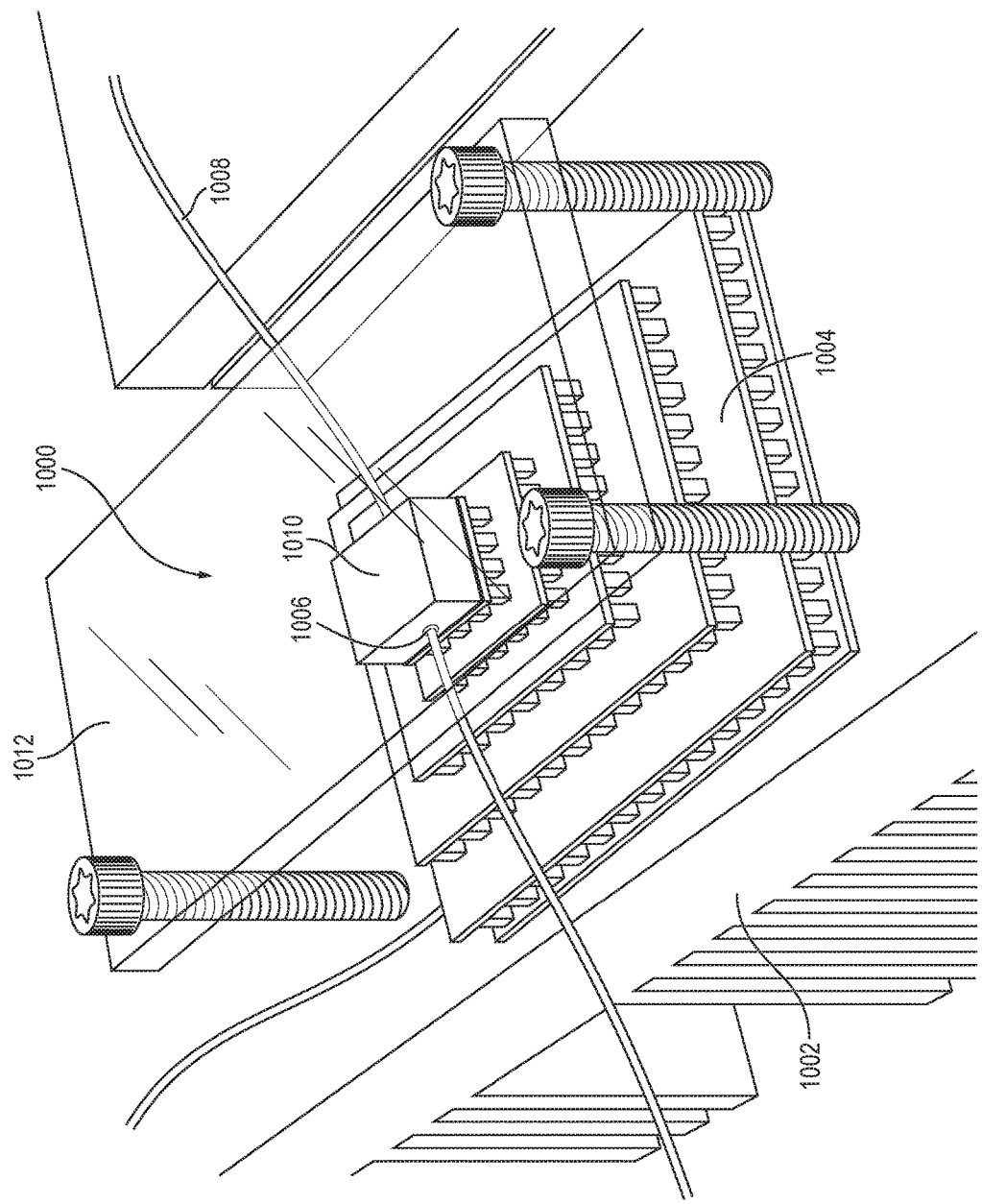

In certain embodiments, the support 100 includes one or more valves coupled to the support 100, the one or more valves being configured to limit (e.g., stop) movement of fluid within an electrokinetic device 110 coupled to the support 100. Suitable valves can substantially lack internal dead space (i.e., space within the valve that is accessible to fluid but experiences very little fluid flux when fluid is flowing through the valve). In certain embodiments, at least one of the one or more valves is a thermally controlled flow controller, such as a freeze valve. FIGS. 10 and 11 depict a thermally controlled flow controller 1000 for use with a support 100 according to one embodiment of the invention. The flow controller 1000 includes a temperature regulation device 1004, a thermally conductive interface 1006, and a flow segment (hidden) of a fluid line 1008. The temperature regulation device 1004 can include one or more Peltier thermoelectric devices (e.g., a stack of two, three, four, five, or more Peltier devices). The thermally conductive interface 1006 may be made from a material having high thermal conductivity that is resistant to thermal damage, such as a metal (e.g., copper). The thermally conductive interface 1006 can wrap around the flow segment of the fluid line 1008. The thermally conductive interface 1006 can be, for example, a sleeve or other object that completely surrounds the flow segment of the fluid line 1008, or it can have a grooved surface that accommodates the flow segment of the fluid line 1008 within its groove. The fluid in the fluid line 1008 may be a liquid that freezes solid at a temperature achievable by the flow controller 1000. The thermally conductive interface 1006 is disposed adjacent the temperature regulation device 1004, preferably in contact with a thermally conductive surface thereof to increase the efficiency of the flow controller 1000.

In certain embodiments, the thermally controlled flow controller 1000 can include a heat sink 1002, which may be made of one or more materials having a high thermal conductivity (and low thermal capacitance), such as aluminum. Alternatively, the flow controller 1000 can be configured to rest on and/or be secured to a heat sink 1002. In addition, the flow controller 1000 can include insulating material 1010, which may be configured to prevent moisture from interfering with the function of the flow controller 1000, which can happen when moisture condenses on the thermally conductive interface 1006 and/or temperature regulation device 1004. The flow controller 1000 can also include a cover 1012 or other device (e.g., a clamp) configured to hold the thermally conductive interface 1006 against the temperature regulation device 1004 and, e.g., thereby increase the efficiency of the flow controller 1000.

Figure 12:
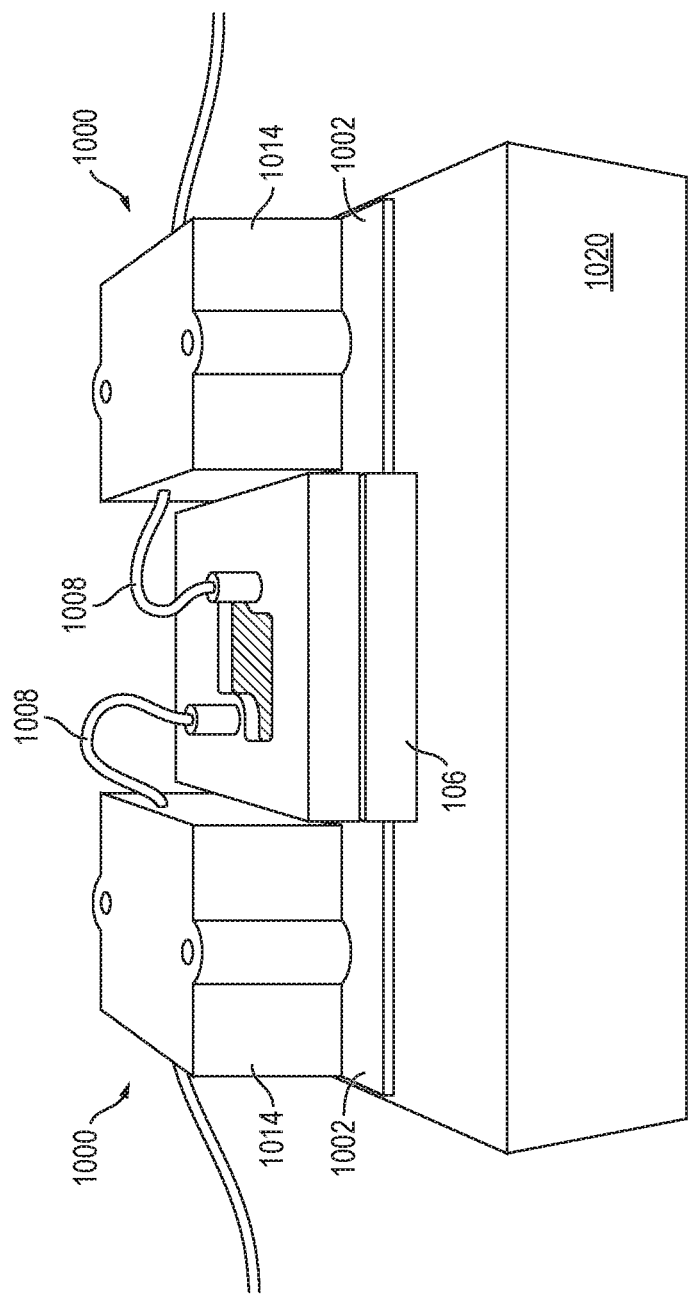
FIG. 12 is a perspective view of a pair of freeze valves, according to some embodiments of the invention. As shown, the freeze valves are flanking a socket that is holding an electrokinetic device.

FIG. 12 depicts a socket 106 and a pair of valves, each a thermally controlled flow controller 1000, according to another embodiment. The flow controllers 1000 are disposed directly upstream and downstream of the socket 106. As shown in FIG. 12, each flow controller 1000 includes a heat sink 1002, and an enclosure 1014. Each enclosure 1014 contains a temperature regulation device 1004, a thermally conductive interface 1006, and a flow segment of a fluid line 1008. The fluid lines 1008 can be seen exiting from the flow controllers 1000 and entering the socket 106. The enclosures 1014 may be made from a material having a low thermal conductivity and/or a low gas permeability. The material can be, for example, PVC. The enclosures 1014 may each have a volume of at least twice (e.g., 2 to 10 times, 2 to 7 times, 2 to 5 times, 2 to 4 times, or 2 to 3 times) the volume of the respective temperature regulation devices 1004 contained therein. The enclosures can be configured to prevent moisture from interfering with the function of the flow controllers 1000, which can happen when moisture condenses on the respective temperature regulation devices 1004 and/or thermally conductive interfaces 1006. FIG. 12 also depicts a secondary heat sink 1020 upon which the flow controllers 1000 are mounted. The secondary heat sink 1020 is configured to absorb heat from the heat sinks 1002 of the flow controllers 1000.

Figure 13:
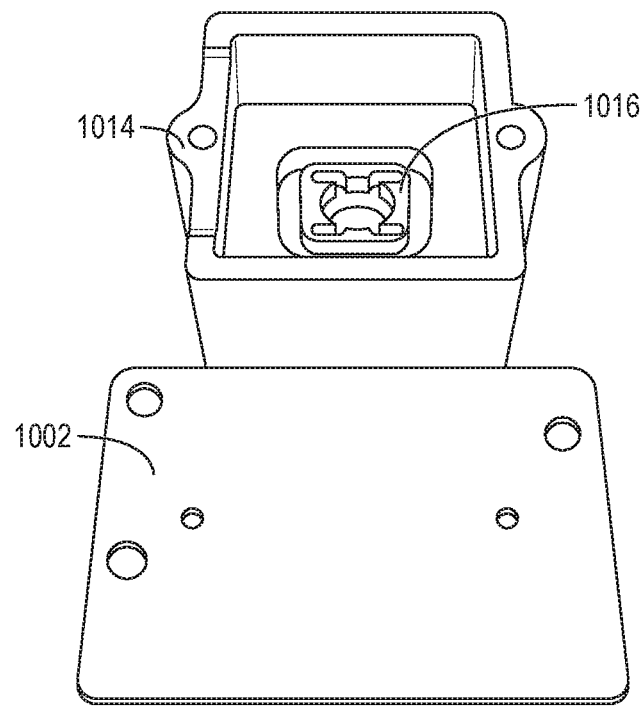
FIG. 13 is a perspective view of various components of the freeze valve depicted in FIG. 12.

FIG. 13 depicts the heat sink 1002 and enclosure 1014 of a thermally controlled flow controller 1000 like the ones depicted in FIG. 12. The underside of the enclosure 1014 is visible in FIG. 13, showing grooves 1016 configured to accommodate the fluid line 1008 (not shown) and/or at least part of the thermally conductive interface 1006. The grooves 1016 can be further configured to hold the thermally conductive interface 1006 (not shown) against the temperature regulation device 1004 (e.g., one or more (e.g., a stack of) Peltier thermoelectric devices; not shown).

Figure 14:
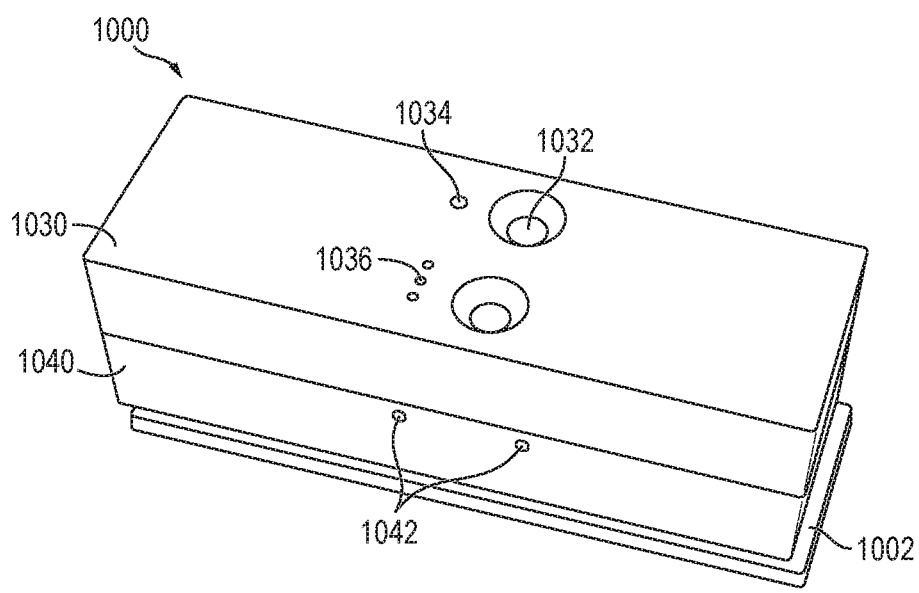
FIG. 14 is a perspective view of a freeze valve, according to some embodiments of the invention.

FIG. 14 depicts the exterior of a thermally controlled flow controller 1000 according to still another embodiment. As shown, the flow controller 1000 includes a cover 1030, a bottom portion 1040, and a heat sink 1002. The cover 1030 defines respective pluralities of indicator openings 1034, 1036 configured to allow indicators (e.g., LEDs) to be observed from a position external to the cover 1030. The indicators can be configured to indicate whether the flow controller 1000 is on or off and/or whether the flow segment of the fluid line 1008 is in an open (i.e., not frozen) or closed (i.e., frozen) configuration. In addition, the cover 1030 can define fastener openings 1032 configured to admit fasteners (e.g., screws) for assembly of the flow controller 1000. The bottom portion 1040 defines a plurality of fluid line openings 1042 configured to admit fluid lines (not shown) into the interior of the bottom portion 1040.

Figure 15:
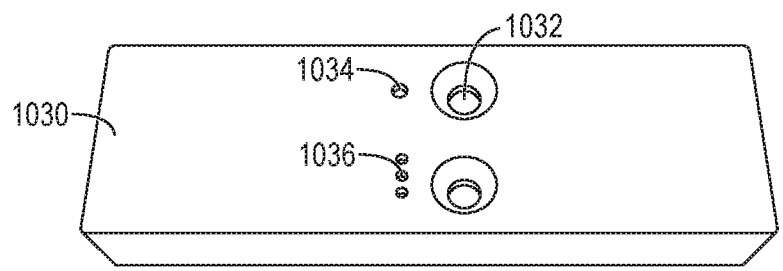
FIGS. 15 and 16 are top and bottom perspective views of a cover of the freeze valve depicted in FIG. 14.
Figure 16:
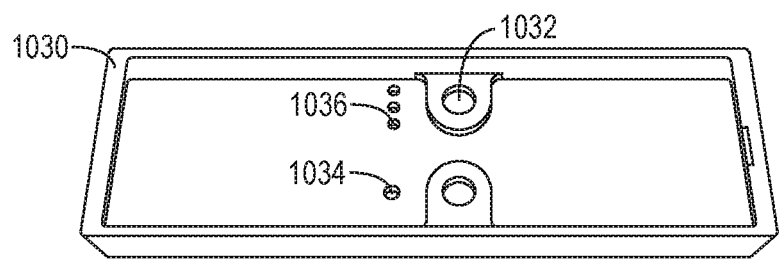

FIGS. 15 and 16 depict the top and the bottom, respectively, of the cover 1030 depicted in FIG. 14, shown without the bottom portion 1040. The indicator openings 1034, 1036 and the fastener openings 1032 are also depicted in FIGS. 15 and 16. FIG. 16 also depicts a cavity formed in the underside of the cover 1030, which is configured to hold a PCB (not shown) of the thermally controlled flow controller 1000. The PCB can include circuitry configured to control one or more temperature regulation devices 1004 (not shown) and/or one or more indicators (not shown). The cover 1030 can be made from a low thermal conductivity material, such as PVC.

Figure 17:
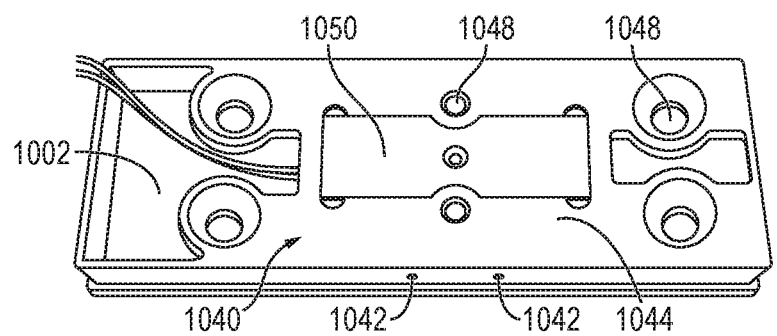
FIG. 17 is a perspective view of a bottom portion of the freeze valve depicted in FIG. 14.
Figure 18:
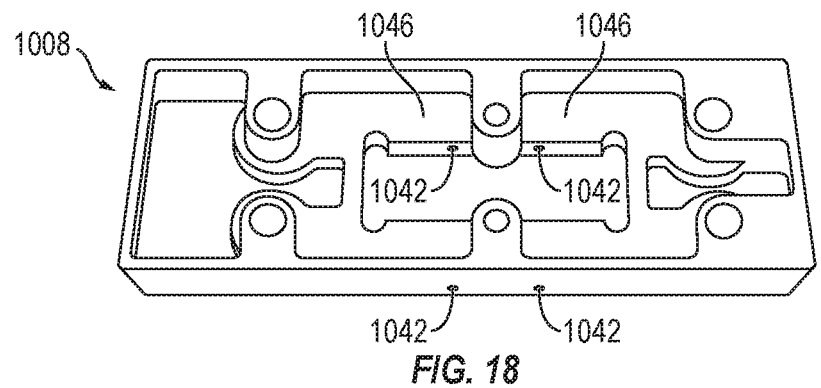
FIG. 18 is a perspective view of an enclosure of the bottom portion of the freeze valve depicted in FIG. 17.
Figure 21:
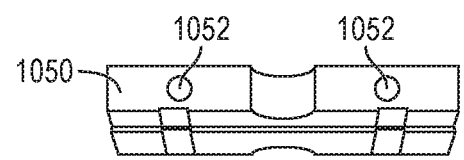

FIG. 17 depicts the bottom portion 1040 and the heat sink 1002 of the thermally controlled flow controller 1000 depicted in FIG. 14, shown without the cover 1030. The bottom portion 1040 includes a sleeve 1050 and an enclosure 1044 configured to hold the sleeve 1050. The bottom portion 1040 also defines fastener openings 1048 configured to admit fasteners (e.g., screws) for mounting the cover 1030 and the bottom portion 1040 on the heat sink 1002. In addition to holding the sleeve 1050, the enclosure 1044 also defines a plurality of fluid line openings 1042 (shown in FIG. 18), which correspond to a plurality of fluid line openings 1052 in the sleeve 1050 (as shown in FIG. 21). The fluid line openings 1042 pass completely through the enclosure 1044 in the horizontal plane of the enclosure 1044. FIG. 18 is a perspective view of the enclosure 1044 from below. The angle of the perspective view shows two corresponding sets of fluid line openings 1042 and two cavities 1046 formed in the underside of the enclosure 1044. The cavities 1046 in the enclosure 1044 are each configured to hold a temperature regulation devices 1004 (e.g., each having one or more (e.g., a stack of two or more) Peltier thermoelectric devices; not shown) and wiring associated therewith (not shown).

Figure 19:
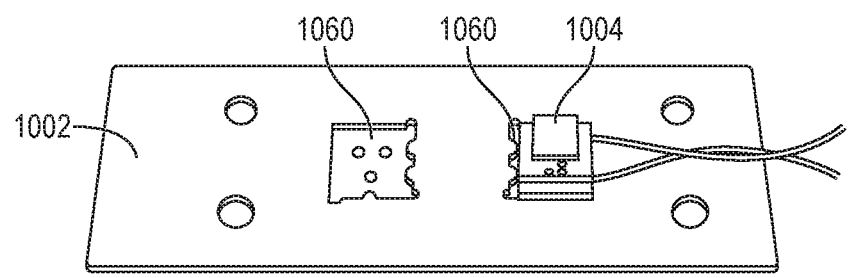
FIG. 19 is a perspective view of a heat sink of the freeze valve depicted in FIG. 14.

FIG. 19 depicts the heat sink 1002, which defines two cavities 1060, each configured to hold a temperature regulation device 1004 (e.g., having one or more (e.g., a stack of two or more) Peltier thermoelectric devices). The heat sink 1002 is also configured to be coupled to a support 100, which may function as a secondary heat sink.

Figure 20:
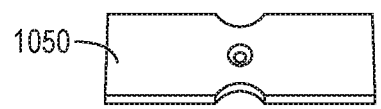
FIGS. 20 and 21 are top and side views of a sleeve of the freeze valve depicted in FIG. 14.

FIGS. 20 and 21 depict a sleeve 1050 configured to hold two fluid lines 1008 (e.g., an inlet and an outlet; not shown). The sleeve 1050 may be configured to completely enclose the flow segments of the fluid lines 1008. Alternatively, the sleeve 1050 can have grooves configured to accommodate the flow segments of the fluid lines 1008. Thus, the sleeve 1050 is an embodiment of a thermally conductive interface 1006. Accordingly, the sleeve 1050 facilitates maintaining the flow segments of the fluid lines 1008 in proximity to the temperature regulation device 1004 (not shown). The sleeve 1050 may be made of a high thermal conductivity (and low thermal capacitance) material, such as copper. The side view in FIG. 21 shows the fluid line 1008 openings 1052 defined by the sleeve 1050. As shown, the fluid line openings 1052 pass completely through the sleeve 1050 in the horizontal plane of the sleeve 1050. The fluid line openings 1052 are substantially aligned with corresponding fluid line openings 1042 in the enclosure 1044 (as shown in FIG. 18), such that, when the sleeve 1050 is disposed in the enclosure 1044 (as shown in FIG. 17), the fluid lines 1008 can pass through both the enclosure 1044 and the sleeve 1050. Further, when the sleeve 1050 is disposed in the enclosure 1044 (as shown in FIG. 17), the sleeve 1050 is placed into contact with the tops of both temperature regulation devices 1004 (e.g., each which can include one or more (e.g., a stack of two or more) Peltier thermoelectric devices; not shown).

In certain embodiments, the thermally controlled flow controller 1000 also includes a thermistor (not shown). The thermistor is configured to monitor the temperature of the sleeve and/or the temperature regulation device 1004 (or a surface thereof). The monitored temperature can provide feedback to indicate the open or closed condition of the flow controller 1000.

In certain embodiments, the thermally controlled flow controller 1000 also includes or is operatively coupled to a printed circuit board (PCB; not shown), as discussed above. The PCB can be configured to interface with the thermistor. The PCB may also be configured to regulate the current (e.g., DC) delivered to the temperature regulation devices 1004. Further, the PCB may be configured to step down the current delivered to the temperature regulation devices 1004.

The thermally controlled flow controllers 1000 described above are robust and have substantially eliminated dead spaces (compare to other fluid valves) in which bacteria or other debris can accumulate and/or grow. Further, the flow controllers 1000 reduce microbial contamination associated with other types of valves. Moreover, the flow controllers 1000 limit movement of fluid within a microfluidic device (e.g., an electrokinetic microfluidic device 110) connected thereto, which would otherwise result from flexing of fluid lines connected to the inlets and outlets of the microfluidic device. To optimize the system for minimizing fluid movement within microfluidic devices, the flow controller(s) 1000 should be disposed as close to the inlet and outlets of the microfluidic devices as practical.

In certain embodiments, the support 100 can also include or interface with $O_2$ and $CO_2$ sources configured to maintain culture conditions. In certain embodiments, the support 100 can also include or interface with a humidity monitor/regulator.

The support 100 can have dimensions of about 6 to 10 inches (or about 150 to 250 mm)×about 2.5 to 5 inches (or about 60 to 120 mm)×about 1 to 2.5 inches (or about 25 to 60 mm). Although it can be desirable to keep the dimensions of the support 100 substantially within these exemplary dimensions, depending upon the functionality incorporated into the support 100 the dimensions may be smaller or larger than the exemplary dimensions. Although the exemplary support 100 has been described as including specific components configured for particular functions, supports according to other embodiments may include different components that perform various combinations and sub-combinations of the described functions.

In certain embodiments, the light modulating subsystem 634 comprises one or more of a digital mirror device (DMD), a liquid crystal display or device (LCD), liquid crystal on silicon device (LCOS), and a ferroelectric liquid crystal on silicon device (FLCOS), and. The light modulating subsystem 634 can be, for example, a projector (e.g., a video projector or a digital projector). One example of a suitable light modulating subsystem is the MOSAIC™ system from ANDOR TECHNOLOGIES™. In other embodiments, the light modulating subsystem 634 may include microshutter array systems (MSA), which may provide improved contrast ratios. In still other embodiments, the light modulating subsystem 634 may include a scanning laser device. In certain embodiments, the light modulating subsystem 634 can be capable of emitting both structured and unstructured light.

In certain embodiments, the support 100 and the light modulating subsystem 634 are each individually configured to be mounted on a microscope, such as a standard research-grade light microscope or fluorescence microscope. For example, the support 100 can be configured to mount of the stage of a microscope. The light modulating subsystem 634 can be configured to mount on a port of a microscope.

Accordingly, in certain embodiments, the invention provides methods for converting a light microscope into a microscope configured for operating an electrokinetic device 110. The methods can include the steps of mounting a system that includes a support 100 (e.g., as described herein) and a light modulating subsystem 634 (e.g., as described herein) on a suitable microscope. The support 100 can be mounted onto a stage of said light microscope, and the light modulating subsystem 634 can be mounted onto a port of said light microscope. In certain embodiments, the converted light microscope can be configured to operate an optically actuated electrokinetic device 110 (e.g., an electrokinetic device having an OET and/or OEW configuration).

In other embodiments, the supports 100 and the light modulating subsystems 634 described herein can be integral components of a light microscope. For example, a microscope having an integrated support 100 and an integrated light modulating subsystems 634 can be configured to operate an optically actuated electrokinetic device 110 (e.g., an electrokinetic device having an OET and/or OEW configuration).

In certain related embodiments, the invention provides a microscope configured for operating an electrokinetic device 110. The microscope can include a support 100 configured to hold an electrokinetic device 110, a light modulating subsystem 634 configured to receive light from a first light source and emit structured light, and an optical train. The optical train can be configured to (1) receive structured light from the light modulating subsystem 634 and focus the structured light on at least a first region in an electrokinetic device 110, when the device 110 is being held by the support 100, and (2) receive reflected and/or emitted light from the electrokinetic device 110 and focus at least a portion of such reflected and/or emitted light onto a detector 602. The optical train can be further configured to receive unstructured light from a second light source 622 and focus the unstructured light on at least a second region of the electrokinetic device 110, when the device 110 is held by the support 100. In certain embodiments, the first and second regions of the electrokinetic device 110 can be overlapping regions. For example, the first region can be a subset of the second region.

In certain embodiments, microscopes of the invention can further include one or more detectors 602. The detector 602 can include, but are not limited to, a charge-coupled device (CCD), complementary metal-oxide semiconductor (CMOS), scientific complementary metal-oxide semiconductor (SCMOS), a camera (e.g., a digital or film camera), or any combination thereof. If at least two detectors 602 are present, one detector 602 can be, for example, a fast-frame-rate camera while the other detector 602 can be a high sensitivity camera. The microscope can also include an eye piece configured for visualization by a user. Furthermore, the optical train can be configured to receive reflected and/or emitted light from the electrokinetic device 110 and focus at least a portion of the reflected and/or emitted light on the additional detector 602. The optical train of the microscope can also include different tube lenses for the different detectors 602, such that the final magnification on each detector 602 can be different.

In certain embodiments, the light modulating subsystems 634 of the microscopes of the invention can include one or more of a digital mirror device (DMD), a liquid crystal display/device (LCD), a liquid crystal on silicon device (LCOS), a ferroelectric liquid crystal on silicon device (FLCOS), and scanning laser devices. Furthermore, the DMD, LCD, LCOS, FLCOS, and/or scanning laser devices can be part of a projector (e.g., a video projector or a digital projector). In other embodiments, the light modulating subsystem 634 may include microshutter array systems (MSA), which may provide improved contrast ratios. In certain embodiments, the microscopes of the invention can include an embedded or external controller (not shown) for controlling the light modulating subsystem 634. Such a controller can be, for example, an external computer or other computational device.

In certain embodiments, the systems 600/microscopes of the invention are configured to use at least two light sources 622, 632. For example, a first light source 632 can be used to produce structured light 650, which is then modulated by a light modulating subsystem 634 for form modulated structured light 652 for optically actuated electrokinesis and/or fluorescent excitation. A second light source 622 can be used to provide background illumination (e.g., using unstructured light 654) for bright-field or dark filed imaging. One example of such a configuration is shown in FIG. 6.

The first light source 632 is shown supplying structured light 650 to a light modulating subsystem 634, which provides modified structured light 652 to the optical train of the microscope. The second light source 622 is shown providing unstructured light 654 to the optical train via the beam splitter 624. Modified structured light 652 from the light modulating subsystem 634 and unstructured light 654 from the second light source 622 travel through the optical train together to reach beam splitter 606, where the light 652, 654 is reflected down through the objective 608 (which may be a lens) to the sample plane 610. Reflected and/or emitted light 662, 664 from the sample plane 610 then travels back up through the objective 608, through the beam splitter 606, and to a dichroic filter 604. Light 662, 664 can be modulated, structured light 652 and unstructured light 654, respectively reflected from the sample plane 610. Alternatively, light 662, 664 can originate at or below the sample plane 610. Only a fraction of the light 662, 664 reaching the dichroic filter 604 passes through the filter 604 and reaches the detector 602. Depending on how the system is being used, beam splitter 606 can be replaced with a dichroic filter (e.g., for detecting fluorescent emissions originating at or below the sample plane 610).

As depicted in FIG. 6, the second light source 622 emits blue light. Blue light reflected from the sample plane 610 is able to pass through dichroic filter 604 and reach the detector 602. In contrast, structured light coming from the light modulating subsystem 634 gets reflected from the sample plane 610, but does not pass through the dichroic filter 604. In this example, the dichroic filter 604 is filtering out visible light having a wavelength longer than 495 nm. Such filtering out of the light from the light modulating subsystem 634 would only be complete (as shown) if the light emitted from the light modulating subsystem 634 did not include any wavelengths shorter than 495 nm. In practice, if the light coming from the light modulating subsystem 634 includes wavelengths shorter than 495 nm (e.g., blue wavelengths), then some of the light from the light modulating subsystem 634 would pass through filter 604 to reach the detector 602. In such a scenario, the filter 604 acts to change the balance between the amount of light that reaches the detector 602 from the first light source 632 and the second light source 622. This can be beneficial if the first light source 632 is significantly stronger than the second light source 622.

One alternative to the arrangement shown in FIG. 6, which accomplishes the same goal of changing the balance between the amount of light that reaches the detector 602 from the first light source 632 and the second light source 622, is to have the second light source 622 emit red light and the filter 604 filter out visible light having a wavelength shorter than 650 nm.

In certain embodiments, the microscopes (or systems) of the invention further comprise a first light source 632 and/or a second light source 622.

In certain embodiments, the first light source 632 can emit a broad spectrum of wavelengths (e.g., "white" light). The first light source 632 can emit, for example, at least one wavelength suitable for excitation of a fluorophore. The first light source 632 can be sufficiently powerful such that structured light emitted by the light modulating subsystem 634 is capable of activating light actuated electrophoresis in an optically actuated electrokinetic device 110. In certain embodiments, the first light source 632 can include a high intensity discharge arc lamp, such as those including metal halides, ceramic discharge, sodium, mercury, and/or xenon. In other embodiments, the first light source 632 can include one or more LEDs (e.g., an array of LEDs, such as a 2×2 array of 4 LEDs or a 3×3 array of 9 LEDs). The LED(s) can include a broad-spectrum "white" light LED (e.g., the UHP-T-LED-White by PRIZMATIX), or various narrowband wavelength LEDs (e.g., emitting a wavelength of about 380 nm, 480 nm, or 560 nm). In still other embodiments, the first light source 632 can incorporate a laser configured to emit light at selectable wavelengths (e.g., for OET and/or fluorescence).

In certain embodiments, the second light source 622 is suitable for bright field illumination. Thus, the second light source 622 can include one or more LEDs (e.g., an array of LEDs, such as a 2×2 array of 4 LEDs or a 3×3 array of 9 LEDs). The LED(s) can be configured to emit white (i.e., wide spectrum) light, blue light, red light, etc. In some embodiments, the second light source 622 can emit light having a wavelength of 495 nm or shorter. For example, the second light source 622 can emit light having a wavelength of substantially 480 nm, substantially 450 nm, or substantially 380 nm. In other embodiments, the second light source 622 can emit light having a wavelength of 650 nm or longer. For example, the second light source 622 can emit light having a wavelength of substantially 750 nm. In still other embodiments, the second light source 622 can emit light having a wavelength of substantially 560 nm.

In certain embodiments, the optical trains of the microscopes of the invention include a dichroic filter 604 that filters out, at least partially, visible light having a wavelength longer than 495 nm. In other embodiments, the optical trains of the microscopes of the invention include a dichroic filter 604 that filters out, at least partially, visible light having a wavelength shorter than 650 nm (or shorter than 620 nm). More generally, the optical train can also include a dichroic filter 604 configured to reduce or substantially prevent structured light from a first light source 632 from reaching a detector 602. Such a filter 604 can be located proximal to the detector 602 (along the optical train). Alternatively, the optical train can include one or more dichroic filters 604 that is/are configured to balance the amount of structure light (e.g., visible structured light) from the light modulating subsystem 634 and the amount of unstructured light (e.g., visible unstructured light) from the second light source 622 that reaches said detector 602. Such balance can be used to ensure that the structured light does not overwhelm the unstructured light at the detector 602 (or in images obtained by the detector 602).

In certain embodiments, the optical trains of the microscopes of the invention can include an objective 608 configured to focus structured and unstructured light on an electrokinetic device 110, with the objective being selected from a 100×, 60×, 50×, 20×, 10×, 5×, 4×, or 2× objective. These magnification powers are listed for illustration and not intended to be limiting. The objection can have any magnification.

The microscopes of the invention can include any of the supports 100 described herein. Thus, for example, the support 100 can include an integrated electrical signal generation subsystem 138 configured to establish, at least intermittently, a biasing voltage between a pair of electrodes in said electrokinetic device 110 when said device 110 is held by said support 100. Alternatively, or in addition, the support 100 can include a thermal control subsystem 140 configured to regulate the temperature of said electrokinetic device 110 when said device 110 is held by said support 100.

Any system or microscope described herein can further include an electrokinetic device 110. The electrokinetic device 110 can be a microfluidic device 110, such as a microfluidic device 110 configured to support dielectrophoresis or a microfluidic device 110 configured to support electrowetting. The electrokinetic device 110 can be an optically actuated electrokinetic device (e.g., an electrokinetic device having an OET and/or OEW configuration).

Figure 7A:
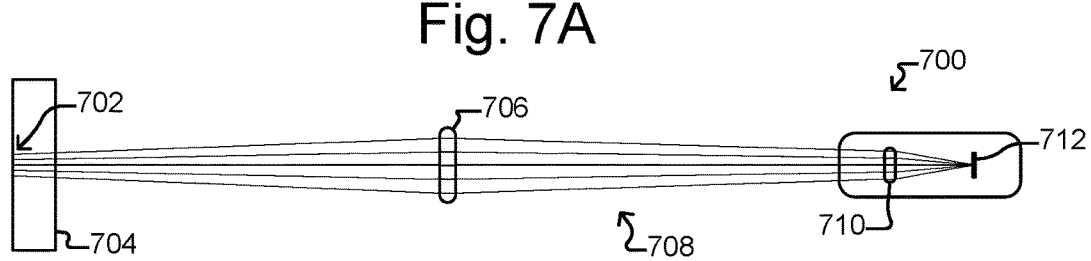
FIGS. 7A-7B are schematic views of a structured light path and an imaging path, respectively, in an optical train according to some embodiments of the invention.

FIG. 7A depicts a structured light path 700 in an optical train according to some embodiments of the invention. The structure light path 700 depicted in FIG. 7A begins at a DMD 702, which includes a glass cover 704 (e.g., a 20 mm glass plate). The DMD 702 may be part of a light modulating subsystem like the light modulating subsystem 634 depicted in FIG. 6. The DMD 702 modifies light from a light source (not shown) to form structured light 708. The structured light 708 is then focused by a tube lens 706 toward an objective 710 (which may be a lens). The objective 710 in turn focuses the structured light 708 onto a cover 712 (e.g., a cover glass). The cover 712 may be a cover of an electrokinetic device 110, such as an optically actuated electrokinetic device. In the latter embodiment, the structure light can actuate and/or operate the optically actuated electrokinetic device 110 as described below.

Figure 7B:
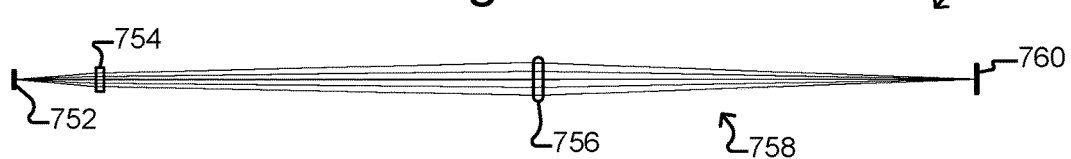

FIG. 7B depicts an imaging light path 750 in an optical train according to some embodiments of the invention. The imaging light path 750 depicted in FIG. 7B begins at a sample plane 752, which may coincide with the cover 712 of an electrokinetic device 110. The sample plane 752 may be similar to the sample plane 610 depicted in FIG. 6. Therefore, the light 758 in the imaging light path 750 may be reflected from the sample plane 752. Alternatively, the light 758 pay have passed through the sample plane 752. From the sample plane 752, the light 758 is focused by an objective lens 754 and an achromatic tube lens 756 toward a camera plane 760. The camera plane 760 can coincide with a detector (not shown), like the detector 602 shown in FIG. 6. In this manner, the imaging light path 750 can be used to visualize a sample or a portion thereof disposed at the sample plane 752 (e.g., contained within an electrokinetic device 110).

Figure 22:
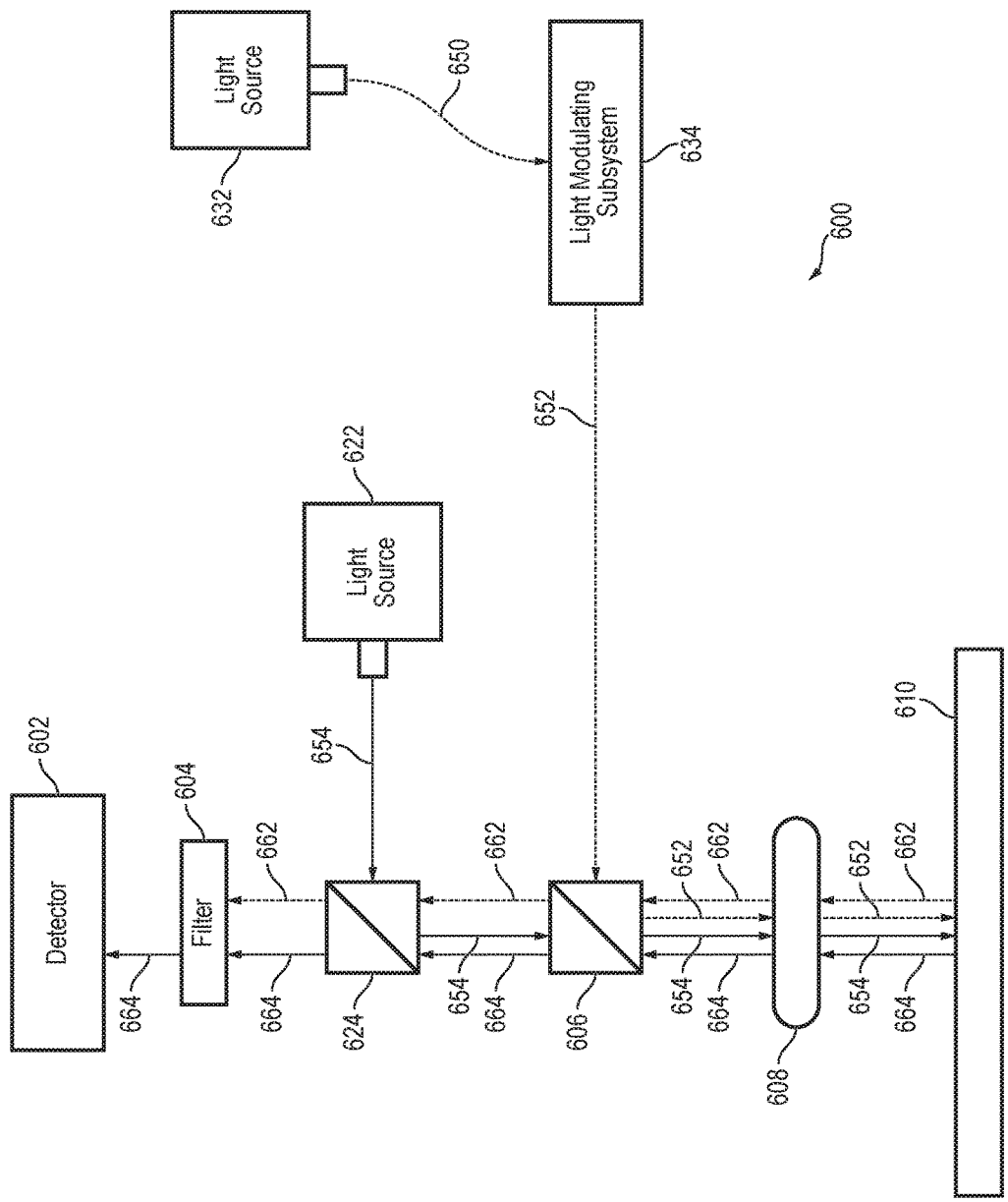
FIG. 22 is a schematic view of a system for operating an electrokinetic microfluidic device, according to some embodiments of the invention. The system depicted in FIG. 22 includes an optical train having various beam-splitters and/or dichroic filters, a first light source, a second light source, a light modulating subsystem, an objective, and a detector.

FIG. 22 depicts a system 600 having an optical train similar to the one depicted in FIG. 6. In the system 600 depicted in FIG. 22, the second light source 622 and the beam splitter 624 are disposed in the main light path between the sample plane 610 and the detector 602, instead of beside the main light path as in FIG. 6. In such embodiments, the second light source is sized, shaped and configured such that it does not interfere with the reflected and/or emitted light 662, 664 from the sample plane 610. Further, the beam splitter 624 may only act as a filter to modify the unstructured light 654 from the second light source 622 without changing the direction of the unstructured light 654. In other embodiments, system 600 may not include the beam splitter 624.

In certain embodiments, the second light source 622 comprises a light pipe and/or one or more LEDs (e.g., an LED array, such as a 2×2 of 3×3 array of LEDs).

Figure 23:
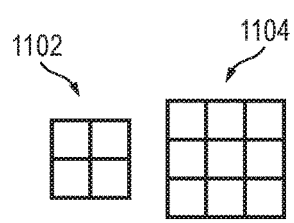
FIG. 23 is a schematic view of two LED arrays, according to some embodiments of the invention.

FIG. 23 depicts two LED arrays that may be used as light sources in the systems 600 described herein. A first LED array 1102 includes a 2×2 array of four LEDs. A second LED array 1104 includes a 3×3 array of nine LEDs. Square arrays produce higher light intensity per unit area compares to non-square arrays. The LEDs in the arrays can have the same color/wavelength (e.g., ultraviolet, 380 nm, 480 nm or 560 nm). Alternatively, various subsets of the LEDs in the arrays can have different colors/wavelengths. Further, LEDs can natively emit a narrowband wavelength (e.g., a 450 nm wavelength), but be coated with a phosphorescent material to emit white light upon excitation with the narrowband wavelength.

Figure 24:
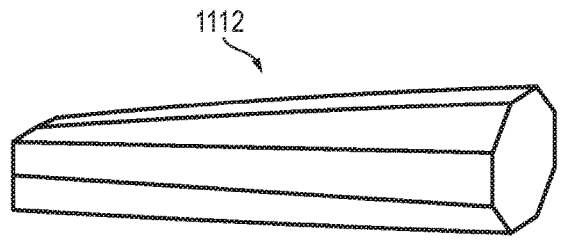
FIG. 24 is a schematic view of a light pipe/optical integrator, according to some embodiments of the invention.

FIG. 24 depicts a light pipe (or optical integrator) 1112, which may be configured to receive and propagate light from a light source, such as one of the LED arrays 1102, 1104 depicted in FIG. 23. Light pipes 1112, also known as "non-imaging collection optics," are configured to propagate light from one end thereof (i.e., an input aperture) to the other end thereof (i.e., an output aperture), with the light emitted from the output aperture being of substantially uniform intensity (i.e., the flux of light through a first area of defined size at the plane of the output aperture is substantially the same as the flux of light through any other area at the plane of the output aperture having the same defined size). The body walls of the light pipe 1112 can be constructed from transparent glass or a transparent plastic. Light pipes 1112 are available, e.g., from EDMOND OPTICS.

Figure 25:
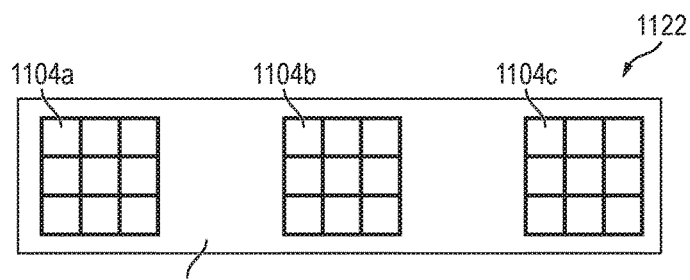
FIG. 25 is a schematic view of a light source, according to some embodiments of the invention.

FIG. 25 depicts a light source 1122 including a plurality of 3×3 LED arrays 1104a-c coupled to a surface 1124. The surface 1124 may be an LED board. The light source 1122 may be disposed within a system such that it is movable relative to an aperture configured to receive light emitted from the light source 1122. For example, the system can comprise a light pipe/optical integrator 1112, and an input aperture of the light pipe 1112 can be configured to receive light emitted from one of the plurality of LED arrays 1104a-c coupled to the surface 1124. Accordingly, different LED arrays 1104a-c may be available as a light source (e.g., through the light pipe /optical integrator 1112) depending on the relative positions of the surface 1124 of the light source 1122 and the light pipe /optical integrator 1112.

Figure 26:
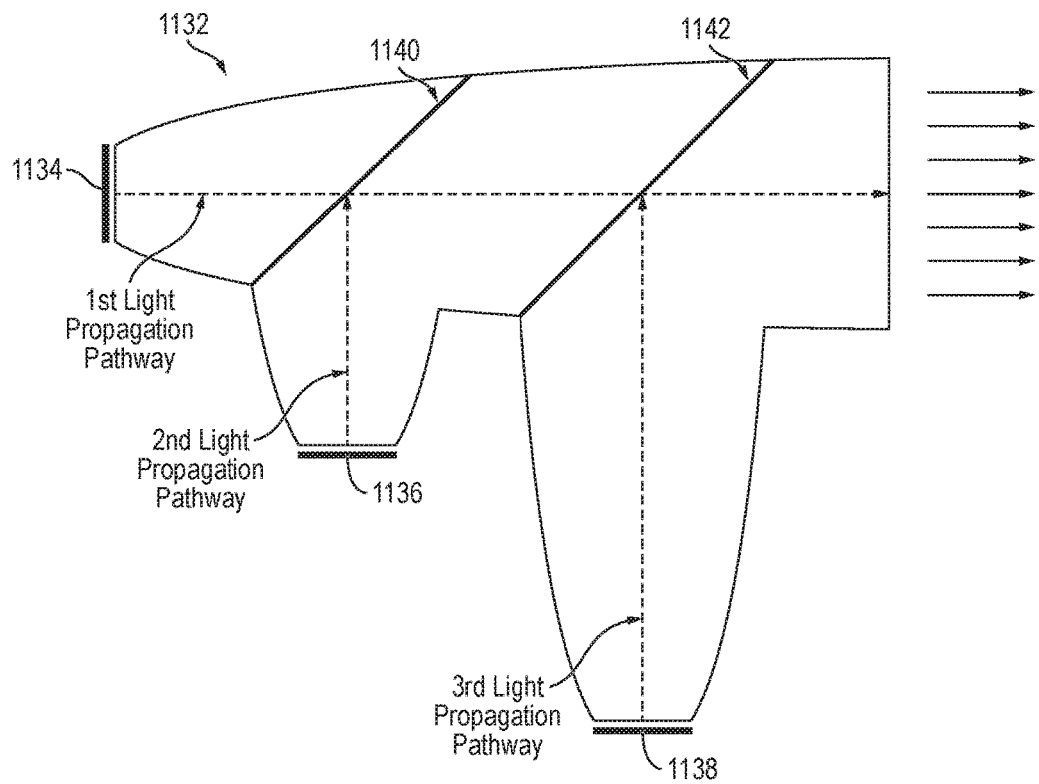
FIG. 26 is a schematic view of a multi-input light pipe/optical integrator, according to some embodiments of the invention.

FIG. 26 depicts a multi-input light pipe/optical integrator 1132. The multi-input light pipe 1132 has a plurality (e.g., 3) of input apertures, each associated with a light propagation pathway and respective light source 1134, 1136, 1138, and one fewer (e.g., 2) dichroic filters 1140, 1142. Each dichroic filter 1140, 1142 is configured to reflect light from a corresponding light source 1136, 1138. The multi-input light pipe 1132 depicted in FIG. 26 has first, second and third light sources 1134, 1136, 1138, any of which may be an array of LEDs (e.g., a 2×2 or 3×3 array of LEDs). The first light source 1134 may be an array of LEDs emitting light at around 380 nm. The second light source 1136 may be an array of LEDs emitting light at around 480 nm. The third light source 1138 may be an array of LEDs emitting light at around 560 nm. Therefore, the wavelength of light exiting from the multi-input light pipe 1132 can be controlled by selectively activating the first, second and third light sources 1134, 1136, 1138. The multi-input light pipe 1132 is configured such that light from any one of the light sources 1134, 1136, 1138, or any combination thereof, entering the corresponding input aperture(s) will be of substantially uniform intensity when it is emitted from the output aperture. The body walls of the multi-input light pipe 1132 can be constructed from transparent glass or a transparent plastic.

Figure 8A:
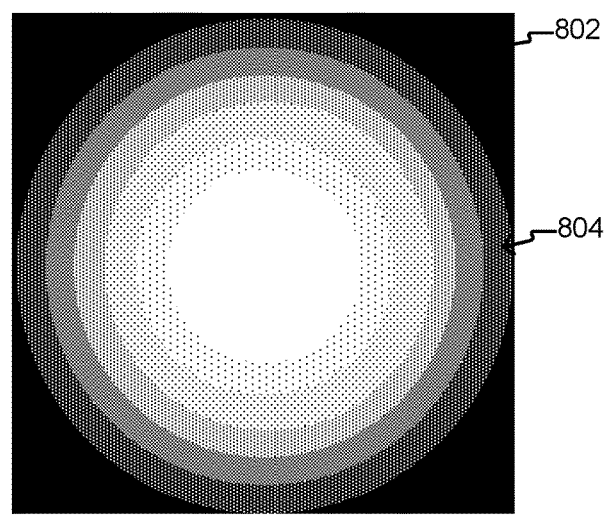
FIGS. 8A-8C are diagrams illustrating how structured light can be used to compensate for optical vignetting.
Figure 8B:
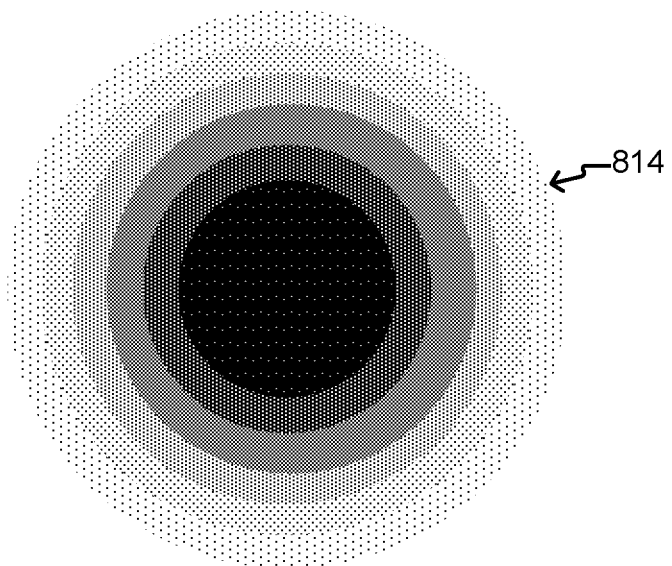
Figure 8C:
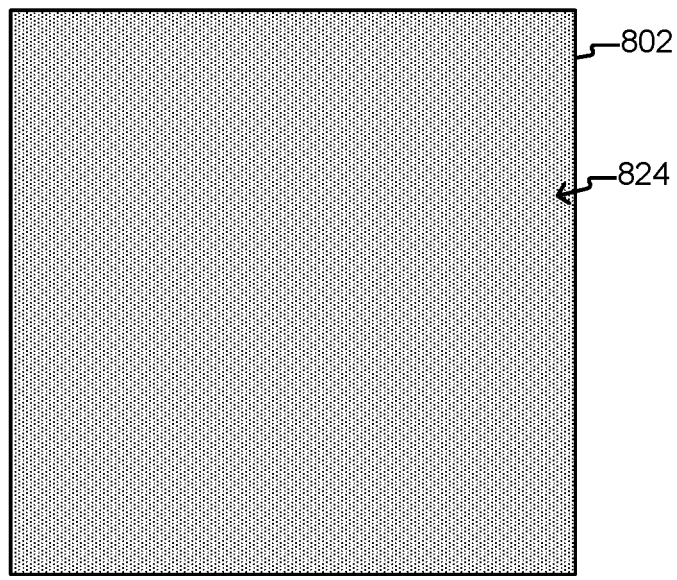

In certain embodiments, the microscopes of the invention are configured to use a single light source (e.g., a white-light LED; not shown) which is received by the light modulating subsystem 634 and transmitted to the optical train. The single light source can be used to provide structured light for light actuated electrokinesis, fluorophore excitation, and bright field illumination. In such an arrangement, structured illumination can be used to compensate for optical vignetting or any other arbitrary non-uniformity in illumination. Optical vignetting is the gradual falloff of illumination 804 toward the edge of a field of view 802 (e.g., FIG. 8A). The light intensity of the single light source can be measured pixel by pixel and the information used to generate an inverted optical vignetting function 814 (e.g., FIG. 8B). The inverted optical vignetting function 814 can then be used to adjust the output of light from the light modulating subsystem, thereby producing a uniformly illuminated field 824 in the field of view 802 (e.g., FIG. 8C).

The invention further provides methods of using light to manipulate a micro-object in an optically actuated electrokinetic device 110. The methods include placing an optically actuated electrokinetic device 110 onto the support 100 of any one of the systems or microscopes described herein, disposing a micro-object on or into the optically actuated electrokinetic device 110, focusing structured light from a light modulating subsystem 634 onto a first region on a surface of the optically actuated electrokinetic device 110, and moving the focused structured light to a second region on the surface of the optically actuated electrokinetic device 110. Provided that the micro-object is located proximal to said first region, moving the focused light can induce the directed movement of the micro-object. The focused structured light can be used, for example, to create a light cage around the micro-object. Alternatively, the focused structured light can be used to contact, at least partially, a fluidic droplet that contains the micro-object.

In another embodiment of a method of using light to manipulate a micro-object in an optically actuated electrokinetic device 110, a light pattern is spatially fixed, and the optically actuated electrokinetic device 110 is moved relative to the light pattern. For instance, the optically actuated electrokinetic device 110 can be moved using a motorized or mechanical microscope stage, which may be automatically controlled by a computer, manually controlled by a user, or semi-automatically controlled by a user with the aid of a computer. In another similar embodiment, the spatially fixed light pattern can form geometric patterns, such as a "cage" or a box, configured to move micro-objects (e.g., a biological cell or a droplet of solution optionally containing a micro-object of interest) on a steerable stage.

Although particular embodiments of the disclosed invention have been shown and described herein, it will be understood by those skilled in the art that they are not intended to limit the present invention, and it will be obvious to those skilled in the art that various changes and modifications may be made (e.g., the dimensions of various parts) without departing from the scope of the disclosed invention, which is to be defined only by the following claims and their equivalents. The specification and drawings are, accordingly, to be regarded in an illustrative rather than restrictive sense.

What is claimed is:

1. A system for operating an electrokinetic device, said system comprising:
    a support configured to hold and operatively couple with an electrokinetic device, wherein said support comprises a socket configured to receive and interface with said electrokinetic device;
    an electrical signal generation subsystem configured to apply a biasing voltage across a pair of electrodes in said electrokinetic device when said electrokinetic device is held by, and operatively coupled with, said support;
    a light modulating subsystem configured to emit structured light onto said electrokinetic device when said electrokinetic device is held by, and operatively coupled with, said support;
    a thermal control subsystem configured to regulate a temperature of said electrokinetic device when said electrokinetic device is held by, and operatively coupled with, said support;
    a first fluid line having a distal end configured to be fluidically coupled to an inlet port of said electrokinetic device, and a second fluid line having a proximal end configured to be fluidically coupled to an outlet port of said electrokinetic device, respectively, when said electrokinetic device is held by, and operatively coupled with, said support; and
    at least one flow controller operatively coupled with one or both of said first and second fluid lines, wherein said at least one flow controller comprises a first thermally-controlled flow controller operatively coupled with one of said first fluid line and said second fluid line to selectively allow fluid to flow therethrough.

2. The system of claim 1, wherein said electrical signal generation subsystem comprises a waveform generator configured to generate a biasing voltage waveform to be applied across said electrode pair when said electrokinetic device is held by, and operatively coupled with, said support.

3. The system of claim 2, wherein said electrical signal generation subsystem further comprises a waveform amplification circuit configured to amplify the biasing waveform generated by said waveform generator, and an oscilloscope configured to measure the biasing voltage waveform, wherein data from said measurement is provided as feedback to said waveform generator.

4. The system of claim 1, said thermal control subsystem comprising a thermoelectric power module, a Peltier thermoelectric device, and a cooling unit, wherein said thermoelectric power module is configured to regulate a temperature of said Peltier thermoelectric device, and wherein said Peltier thermoelectric device is interposed between a surface of said electrokinetic device and a surface of said cooling unit.

5. The system of claim 4, wherein said Peltier thermoelectric device and said thermoelectric power module are mounted on and/or integrated with said support.

6. The system of claim 1, wherein said support further comprises a microprocessor that controls one or both of said electrical signal generation subsystem and said thermal control subsystem.

7. The system of claim 6, wherein said support comprises a printed circuit board (PCB), and wherein at least one of said electrical signal generation subsystem, said thermoelectric power module, and said microprocessor are mounted on and/or integrated with said PCB.

8. The system of claim 6, further comprising an external computational device operatively coupled with said microprocessor, wherein said external computational device comprises a graphical user interface configured to receive operator input and for processing and transmitting said operator input to said microprocessor for controlling one or both of said electrical signal generation subsystem and said thermal control subsystem.

9. The system of claim 8, wherein the microprocessor is configured to transmit to said external computational device data and/or information sensed or received, or otherwise calculated based upon data or information sensed or received, from one or both of said electrical signal generation subsystem and said thermal control subsystem.

10. The system of claim 8, wherein said microprocessor and/or said external computational device are configured to measure and/or monitor an impedance of an electrical circuit across said electrodes of said electrokinetic device when said electrokinetic device is held by, and operatively coupled with, said support.

11. The system of claim 10, wherein said microprocessor and/or said external computational device are configured to determine a flow volume of a fluid path based upon a detected change in the measured and/or monitored impedance of said electrical circuit, said fluid path comprising at least part of a microfluidic circuit within said electrokinetic device.

12. The system of claim 10, wherein said microprocessor and/or said external computational device are configured to determine a height of an interior microfluidic chamber of said electrokinetic device based upon a detected change in the measured and/or monitored impedance of said electrical circuit.

13. The system of claim 10, wherein said microprocessor and/or said external computational device are configured to determine one or more characteristics of chemical and/or biological material contained within the microfluidic circuit of said electrokinetic device based upon a detected change in the measured and/or monitored impedance of said electrical circuit.

14. The system of claim 1, wherein said support and said light modulating subsystem are configured to be mounted on a light microscope.

15. The system of claim 1, wherein said support and said light modulating subsystem are integral components of a light microscope.

16. The system of claim 1, wherein said electrokinetic device is an optically actuated electrokinetic device.

17. The system of claim 1, wherein said first thermally-controlled flow controller comprises a first thermally conductive interface thermally coupled with a flow segment of the first fluid line, and at least one flow control Peltier thermoelectric device configured to controllably lower or raise a temperature of the first thermally conductive interface sufficiently to controllably freeze or thaw fluid contained in the flow segment of the first fluid line and thereby selectively prevent or allow fluid to flow through into or out of the inlet port of said electrokinetic device through the first fluid line.

18. The system of claim 17, wherein said first thermally-controlled flow controller further comprises:
a first housing having a first passageway through which the flow segment of the first fluid line extends, said housing further containing said first thermally conductive interface and the at least one flow control Peltier thermoelectric device; and/or
an insulating material at least partially surrounding the flow segment of the first fluid line proximate the first thermally conductive interface.

19. The system of claim 1, wherein said at least one flow controller comprises a second thermally-controlled flow controller operatively coupled with the other one of said first fluid line and said second fluid line to selectively allow fluid to flow therethrough.

20. The system of claim 1, wherein said first thermally-controlled flow controller comprising
a thermally conductive interface having a first portion thermally coupled with a flow segment of the first fluid line, and a second portion thermally coupled with a flow segment of the second fluid line, and
at least one flow-control Peltier thermoelectric device configured to controllably lower or raise a temperature of the thermally conductive interface sufficiently to controllably freeze or thaw fluid contained in the respective flow segments of the first and second fluid lines and thereby selectively prevent or allow fluid to flow through the first fluid line into the inlet port of said electrokinetic device, or from the outlet port of said electrokinetic device through the outflow fluid line.

21. The system of claim 20, wherein said at least one flow-control Peltier thermoelectric device comprises at least a first flow-control Peltier thermoelectric device thermally coupled to the first portion of the thermally conductive interface proximate the flow segment of the first fluid line, and a second flow-control Peltier thermoelectric device thermally coupled to the second portion of the thermally conductive interface proximate the flow segment of the second fluid line.

22. The system of claim 20, said first thermally-controlled flow controller further comprising a housing having a first passageway through which the flow segment of the first fluid line extends, and a second passageway through which the flow segment of the outflow fluid line extends, wherein the housing defines a thermally insulating chamber in which the thermally conductive interface is mounted.

23. The system of claim 1, wherein said light modulating subsystem comprises a digital mirror device (DMD), a microshutter array system (MSA), a liquid crystal display (LCD), a liquid crystal on silicon device (LCOS), a ferroelectric liquid crystal on silicon device (FLCOS), or a scanning laser device.

24. The system of claim 1, wherein said light modulating subsystem includes a multi-input light pipe, said light pipe comprising:
a housing having a plurality of input apertures, each input aperture configured to receive light emitted from a respective light source, the housing further having an output aperture configured to emit light received through the input apertures;
a first light propagation pathway extending within the housing from a first input aperture to the output aperture;
a first dichroic filter positioned within the housing at an oblique angle across the first light propagation pathway, the first dichroic filter configured and positioned so that light received through the first light aperture passes through the first dichroic filter as it propagates along the first light propagation pathway to the output aperture; and
a second light propagation pathway extending within the housing from a second input aperture to the first dichroic filter, the second propagation pathway and first dichroic filter configured and dimensioned so that light received through the second input aperture propagates along the second light propagation pathway and is reflected onto the first light propagation pathway to the output aperture by the first dichroic filter,
wherein the respective input apertures, first and second light propagation pathways, first dichroic filter, and output aperture are sized, dimensioned and configured such that light emitted by at least one light source and received through at least one of the first and second input apertures is emitted at substantially uniform intensity out the output aperture.

* * * * *